United States Patent
Hama et al.

(10) Patent No.: US 11,443,204 B2
(45) Date of Patent: Sep. 13, 2022

(54) COMPUTER SYSTEM AND METHOD OF PRESENTING INFORMATION ON BASIS OF PREDICTION RESULT FOR INPUT DATA

(71) Applicant: HITACHI, LTD., Tokyo (JP)

(72) Inventors: Naofumi Hama, Tokyo (JP); Masashi Egi, Tokyo (JP); Yasuhide Mori, Tokyo (JP)

(73) Assignee: HITACHI, LTD., Tokyo (JP)

( * ) Notice: Subject to any disclaimer, the term of this patent is extended or adjusted under 35 U.S.C. 154(b) by 471 days.

(21) Appl. No.: 16/702,702

(22) Filed: Dec. 4, 2019

(65) Prior Publication Data
US 2020/0242489 A1 Jul. 30, 2020

(30) Foreign Application Priority Data
Jan. 30, 2019 (JP) .............................. JP2019-014860

(51) Int. Cl.
*G06F 15/00* (2006.01)
*G06F 3/12* (2006.01)
(Continued)

(52) U.S. Cl.
CPC .................. *G06N 5/04* (2013.01); *G06F 3/14* (2013.01); *G06N 20/00* (2019.01)

(58) Field of Classification Search
CPC ............. G06N 5/04; G06N 20/00; G06F 3/14
(Continued)

(56) References Cited

U.S. PATENT DOCUMENTS

2017/0161614 A1* 6/2017 Mehta ..................... G06N 20/00
2018/0158552 A1 6/2018 Liu et al.
(Continued)

FOREIGN PATENT DOCUMENTS

JP 2017-123088 A 7/2017
JP 2018-147280 A 9/2018

OTHER PUBLICATIONS

Scott M. Lundberg, et al., "A Unified Approach to Interpreting Model Predictions," 31 Conference on Neural Information Processing Systems (NIPS 2017), Long Beach, CA, USA, 10 pgs.
(Continued)

*Primary Examiner* — Douglas Q Tran
(74) *Attorney, Agent, or Firm* — Volpe Koenig

(57) ABSTRACT

A computer system stores interpretation factor conversion information for managing an interpretation factor interpreting a basis of a prediction result for input data, the interpretation factor is determined by a value of each of a plurality of feature quantities contained in the input data including values of the plurality of feature quantities, and a first evaluation value of each of the plurality of feature quantities contained in the input data. When evaluation target data is input, the computer system calculates a prediction result, calculates a contribution value of each of the plurality feature quantities contained in the evaluation target data, specifies a corresponding interpretation factor, based on a value and a contribution value of each of the plurality of feature quantities contained in the evaluation target data, by referring to the interpretation factor conversion information, and generates and outputs display information for presenting the specified interpretation factor.

10 Claims, 24 Drawing Sheets

(51) Int. Cl.
    *G06K 1/00*         (2006.01)
    *G06N 5/04*         (2006.01)
    *G06N 20/00*       (2019.01)
    *G06F 3/14*         (2006.01)

(58) Field of Classification Search
    USPC .............................. 358/1.1, 1.15, 1.14, 1.13
    See application file for complete search history.

(56) References Cited

U.S. PATENT DOCUMENTS

| | | | |
|---|---|---|---|
| 2018/0322406 A1 | 11/2018 | Merrill et al. | |
| 2020/0103886 A1* | 4/2020 | Gandenberger | ... G05B 23/0283 |
| 2020/0410672 A1* | 12/2020 | Katscher | ................ G16H 10/60 |

OTHER PUBLICATIONS

Scott M. Lundberg, et al., "Consistent Individualized Feature Attribution for Tree Ensembles," arXiv preprint arXiv: 1802.03888 (2018), 9 pgs.
Michael Grabisch, "k-order additive discrete fuzzy measures and their representation," Fuzzy Sets and Systems 92 (1997), 167-189.
Extended European Search Report dated Jul. 1, 2020 for the European Patent Application No. 19215359.1.
Japanese Office Action dated Jun. 14, 2022 for Japanese Patent Application No. 2019-014860.

* cited by examiner

| ID | CONTRIBUTION VALUE | | | |
|---|---|---|---|---|
| | GENDER | AGE | ... | OCCUPATION |
| 1 | +11.9 | -2.6 | ... | +33.8 |

| INTERPRETATION FACTOR | SCORE |
|---|---|
| INSUFFICIENT REPAYMENT CAPACITY | 17.3 |
| UNSTABLE INCOME | 0.7 |
| ⋮ | ⋮ |

| FEATURE QUANTITY | | | |
|---|---|---|---|
| GENDER | AGE | ... | OCCUPATION |
| U_11 | U_12 | ... | U_1N |

FIG. 11B

K={GENDER}  1100-2

| FEATURE QUANTITY | | | |
|---|---|---|---|
| GENDER | AGE | ... | OCCUPATION |
| V_M1 | U_12 | ... | U_1N |

FIG. 11C

K={AGE}  1100-3

| FEATURE QUANTITY | | | |
|---|---|---|---|
| GENDER | AGE | ... | OCCUPATION |
| U_M1 | V_12 | ... | U_1N |

FIG. 11D

K={GENDER, AGE}  1100-3

| FEATURE QUANTITY | | | |
|---|---|---|---|
| GENDER | AGE | ... | OCCUPATION |
| V_M1 | V_12 | ... | U_1N |

FIG. 11E

K={GENDER, AGE, ... , OCCUPATION}  1100-4

| FEATURE QUANTITY | | | |
|---|---|---|---|
| GENDER | AGE | ... | OCCUPATION |
| V_M1 | V_M2 | ... | V_MN |

FIG. 16

| ID | FEATURE QUANTITY ||||
|---|---|---|---|---|
| | GENDER | AGE | ... | OCCUPATION |
| 1 | V_11 | V_12 | ... | V_1N |

1601: ID
1602: FEATURE QUANTITY
1500

FIG. 17

| ID | REFERENCE ID | SUBSET | FEATURE QUANTITY |||| OUTPUT VALUE |
|---|---|---|---|---|---|---|---|
| | | | GENDER | AGE | ... | OCCUPATION | |
| 1 | 1 | {GENDER, AGE} | V'_11 | V'_12 | ... | V'_1N | +23 |

| FEATURE QUANTITY | DIVISION AREA (VALUE) | DIVISION AREA (CONTRIBUTION VALUE) |
|---|---|---|
| GENDER | AREA 1: MALE<br>AREA 2: FEMALE | AREA 1: 0 OR MORE<br>AREA 2: LESS THAN 0 |
| ⋮ | ⋮ | ⋮ |

| ID 1901 | FEATURE QUANTITY 1902 | AREA (VALUE) 1903 | AREA (CONTRIBUTION VALUE) 1904 | WEIGHT 1905 | NUMBER OF PIECES OF FIRST DATA 1906 | NUMBER OF PIECES OF SECOND DATA 1907 | INTERACTION VALUE 1908 | INTERPRETATION FACTOR 1909 / 1530 |
|---|---|---|---|---|---|---|---|---|
| 1 | GENDER | MALE | LESS THAN 0 | 0.1 | 12(3.8%) | 3(0.9%) | (ID:12, +12); ... (ID:M, +19); | - |
| 1 | YEARS OF SERVICE | LESS THAN AVERAGE VALUE | LESS THAN 0 | 0.8 | | | | |
| 1 | AGE | AVERAGE VALUE OR MORE | LESS THAN 0 | 0.3 | | | | |
| 2 | GENDER | MALE | 0 OR MORE | 0.2 | 34(10.5%) | 2(0.6%) | (ID:3, +13.6); ... (ID:76, +12.7); | - |
| 2 | AGE | AVERAGE VALUE OR LESS | LESS THAN 0 | 0.2 | | | | |
| ... | ... | ... | ... | ... | ... | ... | ... | ... |
| P | YEARS OF SERVICE | AVERAGE VALUE OR MORE | 0 OR MORE | 0.1 | 7(2.2%) | 7(2.2%) | (ID:22, +11.6); ... (ID:41, +18.9); | - |
| P | ANNUAL INCOME | 7,500,000 YEN OR MORE | 0 OR MORE | 0.8 | | | | |
| P | AGE | AVERAGE VALUE OR MORE | LESS THAN 0 | 0.1 | | | | |
| P | WORK PLACE | GENERAL COMPANY | 0 OR MORE | 0.5 | | | | |

FIG. 20

| CONTRIBUTION DEGREE \ VALUE | AVERAGE VALUE OR MORE | LESS THAN AVERAGE VALUE |
|---|---|---|
| +10 OR MORE | ( 3 , 0.7 )   2000-1<br>  2001  2002 | ( 4 , 0.8 )   2000-2 |
| +10 TO 0 | | |
| LESS THAN 0 | ( 10 , 0.7 )   2000-2 | |

1540

| ID | INTERMEDIATE CALCULATION DATA ID | SUBSET | INTERACTION VALUE |
|---|---|---|---|
| 1 | 1 | {GENDER, AGE} | +11 |
| 2 | 1 | {GENDER, ANNUAL INCOME} | -2.3 |
| ⋮ | ⋮ | ⋮ | ⋮ |
| i | 1 | {GENDER, ANNUAL INCOME, YEARS OF SERVICE} | +4.0 |
| ⋮ | ⋮ | ⋮ | ⋮ |
| M | 1 | {AGE, ANNUAL INCOME, YEARS OF SERVICE, ...} | -0.2 |

| ID | ... | INTEGRATION ID | INTEGRATION TYPE |
|---|---|---|---|
| 1 | ... | 1 | NORMAL |
| 2 | ... | - | - |
| 3 | ... | 2 | SPECIAL |
| 4 | ... | 1 | NORMAL |
| 5 | ... | - | - |
| 6 | ... | 2 | SPECIAL |
| ⋮ | ... | ⋮ | ⋮ |
| P | ... | - | - |

FIG. 30

CONFIRMATION SCREEN — 3000

3001
CANDIDATE INTERPRETATION FACTOR: (ID:12, ID:18) — 3011

INDEX: 0.78 — 3012

3002

ID : 12

| FEATURE QUANTITY | YEARS OF SERVICE | WORK PLACE |
|---|---|---|
| AREA (VALUE) | AVERAGE VALUE OR MORE | GENERAL COMPANY |
| AREA (CONTRIBUTION VALUE) | 0 OR MORE | +10 OR MORE |
| WEIGHT | 0.4 | 0.71 |
| NUMBER OF PIECES OF FIRST DATA | 41(12.7%) | |
| NUMBER OF PIECES OF SECOND DATA | 9(2.8%) | |
| INTERACTION VALUE | (ID:12, +12); ... (ID:100, +19); | |

ID : 18

| FEATURE QUANTITY | YEARS OF SERVICE | WORK PLACE |
|---|---|---|
| AREA (VALUE) | AVERAGE VALUE OR MORE | GOVERNMENT OFFICIAL |
| AREA (CONTRIBUTION VALUE) | 0 OR MORE | +10 OR MORE |
| WEIGHT | 0.4 | 0.6 |
| NUMBER OF PIECES OF FIRST DATA | 30(9.3%) | |
| NUMBER OF PIECES OF SECOND DATA | 3(0.9%) | |
| INTERACTION VALUE | (ID:8, +10); ... (ID:87, +21); | |

[INTEGRATE] 3003   [DISCARD] 3004   [NEXT] 3005

[COMPLETE] 3006

COMPUTER SYSTEM AND METHOD OF PRESENTING INFORMATION ON BASIS OF PREDICTION RESULT FOR INPUT DATA

CLAIM OF PRIORITY

The present application claims priority from Japanese patent application JP 2019-014860 filed on Jan. 30, 2019, the content of which is hereby incorporated by reference into this application.

BACKGROUND OF THE INVENTION

1. Field of the Invention

The present invention relates to a system and method of presenting useful data for interpreting a basis for a prediction result of AI that performs a prediction based on a model constructed by machine learning.

2. Description of the Related Art

In recent years, an assistance system that utilizes AI in various fields such as a medical field and a financial field has been provided. For example, in the medical field, the AI is utilized to predict a disease incidence rate (event) of a person (subject) and to specify symptoms. In the financial field, the credit review or the like is performed by utilizing the AI. For example, an occurrence rate (event) of loan loss of an applicant (subject) is predicted.

As a result of advances in technological development aimed at improving accuracy of prediction results output by the AI, such as prediction of disease incidence, the black-box processing of an AI model (algorithm) is accelerated. Therefore, the user who uses the AI cannot trust the predicted value (prediction result) of the AI.

Under such a background, there is an increasing demand for describing a basis of the prediction result of AI and verifying an operation by a developer or an operator of a system utilizing AI.

JP-A-2018-147280 and Lundberg, Scott M., and Su-In Lee. "A unified approach to interpreting model predictions." Advances in Neural Information Processing Systems (pp. 4765-4774). 2017. (Non-Patent Literature 1) provides techniques for presenting information indicating reliability of a system to a user who uses the system.

JP-A-2018-147280 states that "A data analysis device includes a data set generation unit that generates explanatory variable data to be input to a machine learning model and inputs the generated explanatory variable data to the machine learning model to obtain objective variable data; and a model evaluation unit that calculates a relationship between the explanatory variable and the objective variable based on the explanatory variable data and the objective variable data generated by the data set generation unit.".

JP-A-2017-123088 states that "A contribution degree for each explanatory variable is calculated by a decision tree learning algorithm, and groups each having a first predetermined number of first explanatory variables are extracted from a higher rank in descending order of contribution degree."

Non-Patent Literature 1 describes a method of calculating a contribution degree to a predicted value of AI for each feature quantity of evaluation target data by using a combination of a plurality of pieces of intermediate evaluation data generated from the evaluation target data and comparison target data, and predicted values obtained by inputting each perturbation data to the AI.

The relationship between the explanatory variable and the objective variable calculated by the data analysis method in JP-A-2018-147280 and the data calculated in Non-Patent Literature 1 are influence degree on the objective variable for each explanatory variable. However, even if the explanatory variable name and the contribution degree are presented to an end user, the end user hardly understands and interprets the meaning thereof and cannot confirm authenticity of the prediction result by collating job knowledge of the user.

In the technique described in JP-A-2017-123088, the explanatory variable group is extracted in descending order of the contribution degree without using job knowledge possessed by the user. Therefore, the extracted explanatory variable group cannot be interpreted from the viewpoint of the job knowledge of the user.

SUMMARY OF THE INVENTION

The present invention provides a system and method of presenting information useful for a user to interpret a basis of a prediction result output by AI.

A representative example of the invention disclosed in the present application is as follows. That is, the invention provides a computer system including at least one computer that includes a processor and a memory connected to the processor, in which the memory stores model information for predicting an event of a target based on input data including a value of a plurality of feature quantities indicating a state of the target, and interpretation factor conversion information for managing an interpretation factor interpreting a basis of a prediction result for the input data, the interpretation factor being determined by a value of each of the plurality of feature quantities contained in the input data and a first evaluation value of the value of each of the plurality of feature quantities contained in the input data, the first evaluation value showing magnitude of contribution of the value of the feature quantity to a prediction result for the input data, and the processor is configured to calculate, when evaluation target data which is the input data to be evaluated is input, a prediction result for the evaluation target data based on the model information, calculate a first evaluation value of each of the plurality of feature quantities contained in the evaluation target data, specify a corresponding interpretation factor, based on the value and first evaluation value of each of the plurality of feature quantities contained in the evaluation target data, by referring to the interpretation factor conversion information, and generate display information for presenting the specified interpretation factor and output the display information.

According to the aspect of the present invention, data useful for the user to interpret the basis of the prediction result output from AI can be presented. Problems, configurations, and effects other than those described above will be apparent from the following description of the embodiments.

BRIEF DESCRIPTION OF THE DRAWINGS

FIG. 11A shows an example of a data structure of intermediate data according to the first embodiment.

FIG. 11B shows an example of a data structure of intermediate data according to the first embodiment.

FIG. 11C shows an example of a data structure of intermediate data according to the first embodiment.

FIG. 11D shows an example of a data structure of intermediate data according to the first embodiment.

FIG. 11E shows an example of a data structure of intermediate data according to the first embodiment.

FIG. 16 shows an example of a data structure of data for generation according to the second embodiment.

FIG. 17 shows an example of a data structure of intermediate calculation data according to the second embodiment.

FIG. 18 shows an example of a data structure of area division information according to the second embodiment.

FIG. 19 shows an example of a data structure of candidate interpretation factor information according to the second embodiment.

FIG. 20 shows an example of a data structure of a candidate conversion table according to the second embodiment.

FIG. 30 shows an example of an integration confirmation screen displayed on the terminal according to the third embodiment.

DESCRIPTION OF THE PREFERRED EMBODIMENTS

Figure 1:
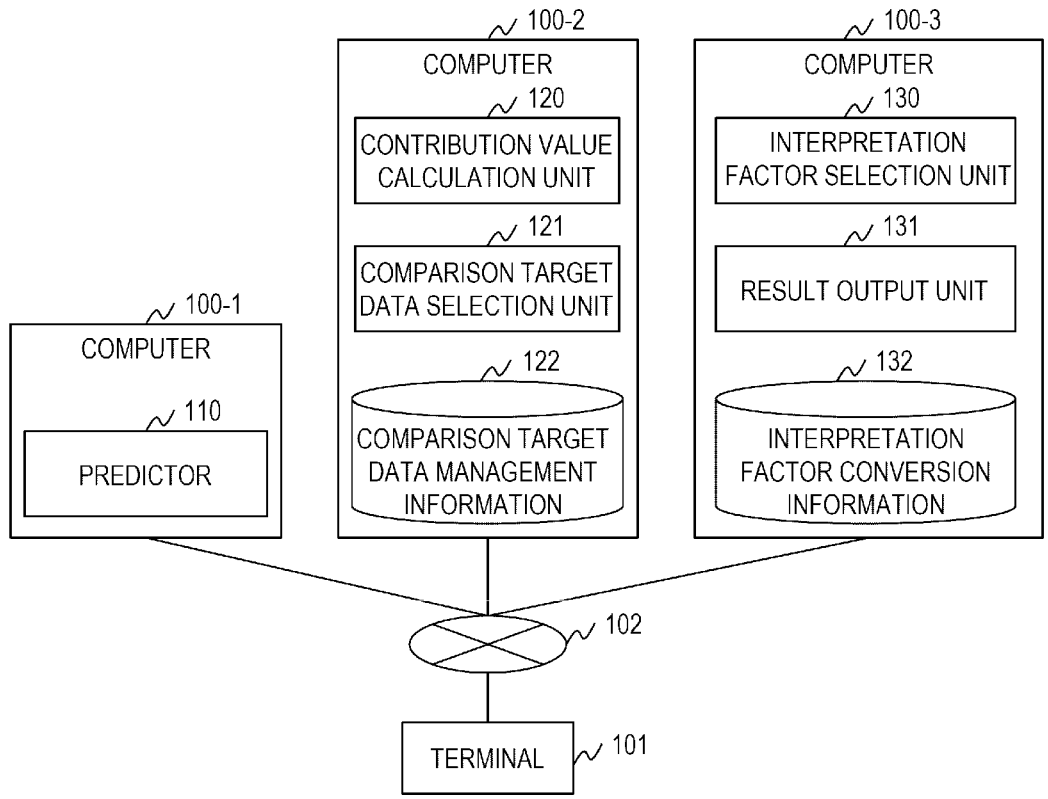
FIG. 1 shows an example of a configuration of a computer system according to a first embodiment.

Hereinafter, embodiments of the invention will be described with reference to the drawings. However, these embodiments are merely examples for implementing the invention, and do not limit the technical scope of the invention. It will be readily understood by those skilled in the art that the specific configuration may be modified without departing from the spirit or scope of the invention.

In configurations according to the invention described below, the same or similar configurations or functions are denoted by the same reference numerals, and repeated descriptions thereof are omitted.

Descriptions such as "first", "second", and "third" in the present specification are used to identify constituent elements and do not necessarily limit the number or the order.

In order to facilitate understanding of the invention, the position, size, shape, range, and the like of each component shown in the drawings may not represent actual position, size, shape, range, and the like. Therefore, the invention is not limited to the position, size, shape, and range disclosed in the drawings.

First Embodiment

FIG. 1 shows an example of a configuration of a computer system according to a first embodiment.

The computer system includes a plurality of computers 100-1, 100-2, and 100-3, and a terminal 101. The plurality of computers 100-1, 100-2, and 100-3 and the terminal 101 are connected to each other via a network 102. The network 102 is, for example, a wide area network (WAN) or a local area network (LAN). A connection method of the network 102 may be either wired or wireless.

In the following description, the computers 100-1, 100-2, and 100-3 are described as a computer 100 when not being distinguished from one another.

The terminal 101 is a computer operated by a user. The terminal 101 is, for example, a personal computer, a smart phone, a tablet terminal, or the like. The terminal 101 inputs, based on an operation of a user, input data and the like necessary for prediction of a target event by AI, and the like. The input data includes values of a plurality of feature quantities. Evaluation target data 300 (see FIG. 3), intermediate data 1100 (see FIG. 11), and data for generation 1500 (see FIG. 15) are examples of the input data.

The terminal 101 includes a processor, a memory, a network interface, an input device, and an output device. The input device is a device such as a keyboard, a mouse, and a touch panel, and the output device is a device such as a touch panel and a display.

The computer 100-1 executes processing for the input data based on a model (algorithm) for predicting an event of a target, and outputs a predicted value (prediction result). The output predicted value is, for example, a classification result of the input data and an occurrence probability of any risk. The computer 100-1 includes a predictor 110.

The predictor 110 performs processing for the input data based on model information defining the model, and outputs a predicted value. The model information is generated by machine learning or the like using learning data. Information on a neural network or a decision tree is stored in the model information.

The computer 100-2 calculates, for a value of each feature quantity contained in the input data, a contribution value (a first evaluation value) which represents magnitude of contribution (magnitude of influence) to a predicted value of a value of a feature quantity. The computer 100-2 includes a contribution value calculation unit 120 and a comparison target data selection unit 121, and stores comparison target data management information 122.

Figure 4:
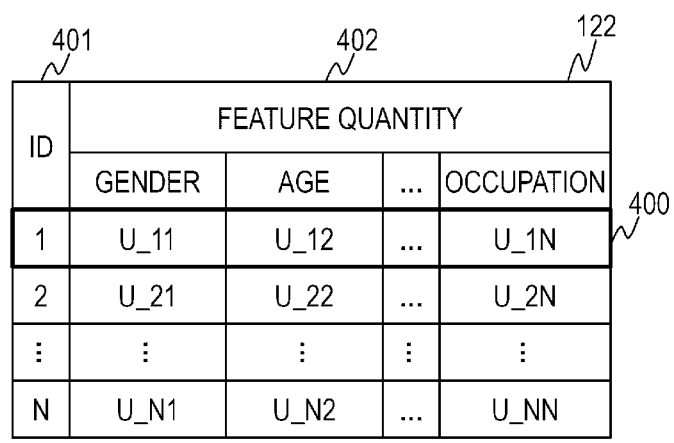
FIG. 4 shows an example of a data structure of management information of comparison target data according to the first embodiment.

The comparison target data management information 122 is information for managing comparison target data 400 (see FIG. 4). Here, the comparison target data 400 is data serving as a reference for characterizing the evaluation target data 300 when calculating a contribution value of each feature quantity of the evaluation target data 300. The learning data may be set as the comparison target data 400, or the comparison target data 400 that is artificially generated using a mode value and an average value of the learning data may be set.

When the contribution value of the feature quantity contained in the evaluation target data 300 is calculated without using the comparison target data 400, the computer 100-2 may not store the comparison target data management information 122.

The contribution value calculation unit 120 calculates, as the contribution value, a value indicating how much the evaluation target data 300 contributes to the predicted value by having such a feature quantity as compared with the comparison target data 400.

The comparison target data selection unit 121 selects, from the comparison target data management information 122, the comparison target data 400 to be used for calculating a contribution value of a feature quantity contained in the evaluation target data 300.

The computer 100-3 outputs information for interpreting a basis of output of a predicted value of the evaluation target data 300. The computer 100-3 includes an interpretation factor selection unit 130 and a result output unit 131 and stores interpretation factor conversion information 132.

The interpretation factor conversion information 132 is information for managing an interpretation factor which is determined by a value and a contribution value of a feature quantity contained in the evaluation target data 300. As to be described below, the computer 100-3 outputs, as information to be presented to the user, information including the interpretation factor and a score. Here, the interpretation factor is a specific factor in accordance with a target or an event of a target. In the present embodiment, natural language information that can be understood by the user is set as an interpretation factor. The score is a value for evaluating validity of the interpretation factor.

The interpretation factor selection unit 130 specifies a corresponding interpretation factor by referring to the interpretation factor conversion information 132 based on the value and the contribution value of the feature quantity, and calculates a score of the interpretation factor.

The result output unit 131 generates display information for presenting information on the predicted value and the interpretation factor of the evaluation target data 300 to the user, and transmits the display information to the terminal 101.

It should be noted that any one of the computers 100-1, 100-2, and 100-3 has an operation receiving unit that provides an application programming interface (API) for receiving a request, data, and the like from the terminal 101.

Figure 2:
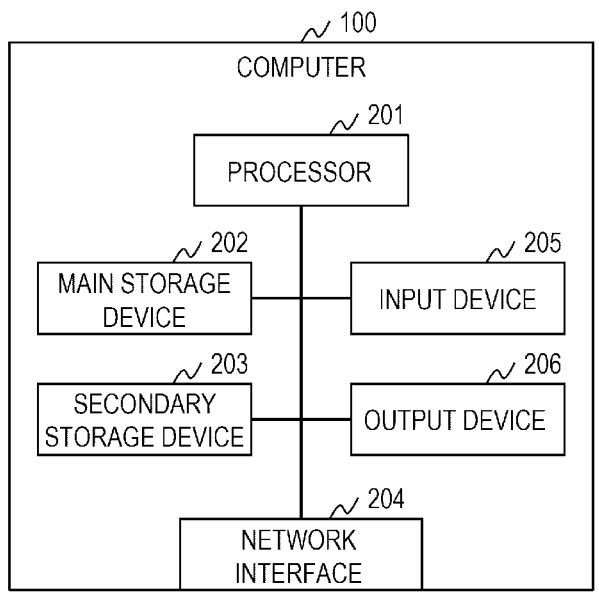
FIG. 2 shows an example of a hardware configuration of a computer according to the first embodiment.

Here, a hardware configuration of the computer 100 will be described. FIG. 2 shows an example of the hardware configuration of the computer 100 according to the first embodiment.

The computer 100 includes a processor 201, a main storage device 202, a secondary storage device 203, a network interface 204, an input device 205, and an output device 206. The respective hardware components are connected to one another via an internal bus. The computer 100 may not include any one of the secondary storage device 203, the input device 205, and the output device 206.

The processor 201 executes a program stored in the main storage device 202. The processor 201 operates as a functional unit (module) that implements a specific function, such as the contribution value calculation unit 120, by executing processing in accordance with the program. In the following description, when processing is described in terms of a functional unit, it is indicated that the processor 201 executes a program that implements the functional unit.

The main storage device 202 stores the program to be executed by the processor 201 and information to be used by the program. The main storage device 202 includes a work area to be temporarily used by the program.

Program and model information for implementing the predictor 110 is stored in the main storage device 202 of the computer 100-1. A program for implementing the contribution value calculation unit 120 and the comparison target data selection unit 121 is stored in the main storage device 202 of the computer 100-2. A program for implementing the interpretation factor selection unit 130 and the result output unit 131 is stored in the main storage device 202 of the computer 100-3. The main storage device 202 of any one of the computers 100-1, 100-2, and 100-3 stores a program for implementing the operation receiving unit.

The secondary storage device 203, such as a hard disk drive (HDD) and a solid state drive (SSD), stores data permanently.

The secondary storage device 203 of the computer 100-2 stores the comparison target data management information 122. The secondary storage device 203 of the computer 100-3 stores the interpretation factor conversion information 132.

For the functional units provided in each of the computers 100, the plurality of functional units may be integrated into one functional unit, or one functional unit may be divided into a plurality of functional units for each function. Each of the functional units may be integrated into one computer 100.

Figure 3:
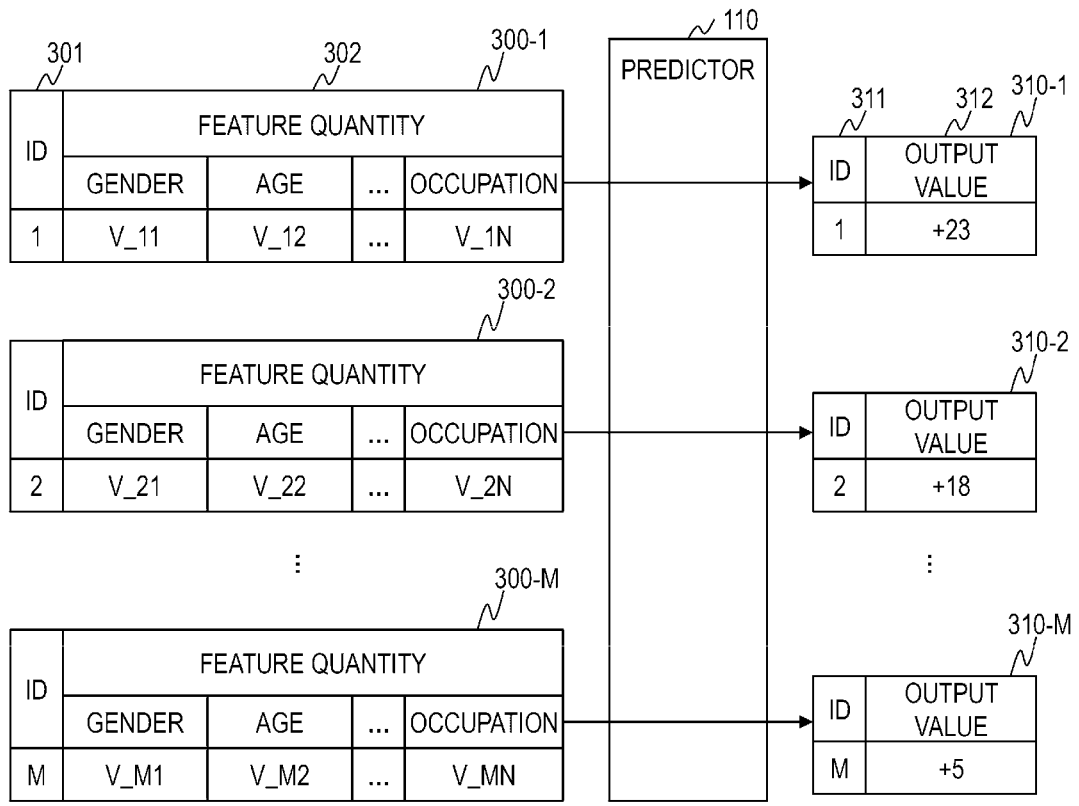
FIG. 3 shows an example of a data structure of evaluation target data and output data according to the first embodiment.

FIG. 3 shows an example of a data structure of the evaluation target data and the output data according to the first embodiment.

The predictor 110 processes the evaluation target data 300 including an ID 301 and feature quantities 302 based on the model information, and outputs output data 310 including an ID 311 and an output value 312 as a prediction result.

In the example shown in FIG. 3, output data 310-1 is output from evaluation target data 300-1, output data 310-2 is output from the evaluation target data 300-2, and output data 310-M is output from evaluation target data 300-M.

A field of the ID 301 stores identification information of the evaluation target data 300. In the ID 301 according to the first embodiment, a number is stored.

A field group of the feature quantity 302 stores values of feature quantities contained in the evaluation target data 300. The feature quantity is, for example, gender, age, annual income, and deposit amount. One of descriptions "male" and "female" is stored in a field of the feature quantity corresponding to the gender, and a numerical value is stored in a field of the feature quantity corresponding to the age.

A field of the ID 311 stores identification information of the output data 310. It is assumed that the same value as that of ID 301 is set in the ID 311. A field of the output value 312 stores a predicted value output by the predictor 110.

FIG. 4 shows an example of a data structure of the comparison target data management information 122 according to the first embodiment.

The comparison target data management information 122 includes an entry 400 including an ID 401 and feature quantities 402. One entry 400 corresponds to one piece of comparison target data. In the following description, the entry 400 is also referred to as comparison target data 400.

A field of the ID 401 stores identification information of the comparison target data 400. In the field of the ID 401 according to the first embodiment, a number is stored. The number stored in the field of the ID 401 is not related to the numbers stored in the field of the ID 301 and the field of the ID 311.

A field group of the feature quantity 402 stores values of feature quantities contained in the comparison target data 400. The feature quantities contained in the field group of the feature quantity 402 are the same as the feature quantities contained in the field group of the feature quantity 302.

Figure 5:
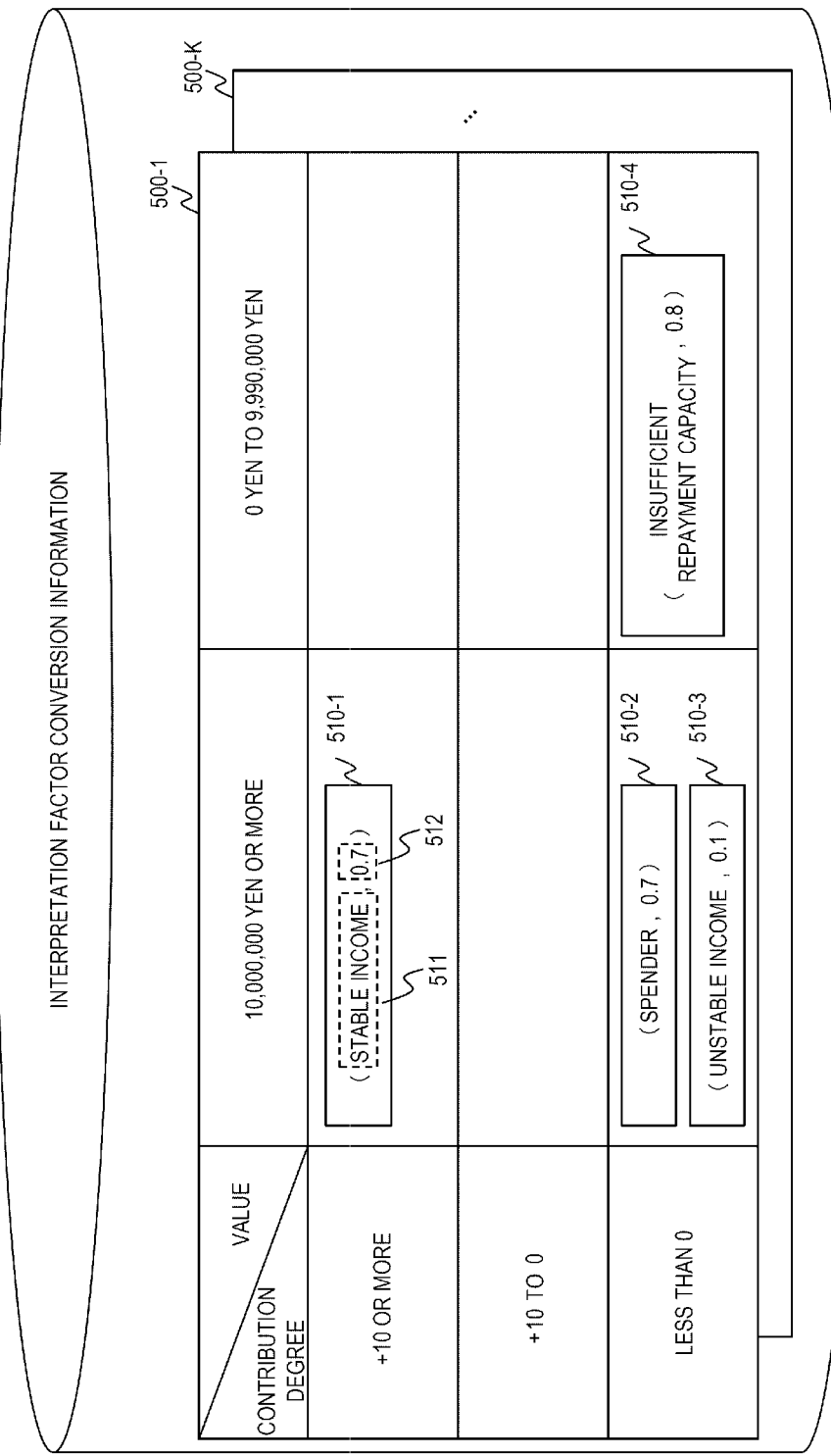
FIG. 5 shows an example of a data structure of interpretation factor conversion information according to the first embodiment.

FIG. 5 shows an example of a data structure of the interpretation factor conversion information 132 according to the first embodiment.

The interpretation factor conversion information 132 is information in which a set including, as elements, a combination of a value and contribution value of the feature quantity contained in the input data is associated with an interpretation factor. The interpretation factor conversion information 132 according to the first embodiment includes a conversion table 500 associated with identification information of the respective feature quantities.

The conversion table 500 denotes data in a row-column format in which an area of a value of a feature quantity is defined as a row component and an area of a contribution value of a feature quantity is defined as a column component. The conversion table 500 denotes information for specifying an interpretation factor by using a set, having one combination as an element, as a retrieval key.

A piece of interpretation factor data 510 is stored in at least one cell of the conversion table 500. It should be noted that two or more pieces of interpretation factor data 510 may be stored in one cell. The interpretation factor data 510 includes an interpretation factor 511 and a weight 512.

The interpretation factor 511 is natural language information. The interpretation factor data 510 including the same interpretation factors 511 is set in the plurality of conversion tables 500, whereby enabling interpretation of an abstraction about what the evaluation target data 300 determined by the value and the contribution value of each feature quantity generally means.

The weight 512 is a value representing the degree of validity corresponding to the interpretation factor. As will be described below, a score of the interpretation factor is calculated using the weight 512. It should be noted that the weight (score) may not be taken into consideration when all the weights 512 of all the conversion tables 500 are set to be the same.

The interpretation factor conversion information 132 may be information that can specify an interpretation factor based on a value and a contribution value of a feature quantity. For example, instead of the conversion table 500, data in a format of a table which stores data in which a set including a plurality of combinations as elements is associated with an interpretation factor, may be used.

It is assumed that the interpretation factor conversion information 132 is set in advance in the first embodiment. A method of generating the interpretation factor conversion information 132 will be described in a second embodiment.

Figures 6, 7, 8:
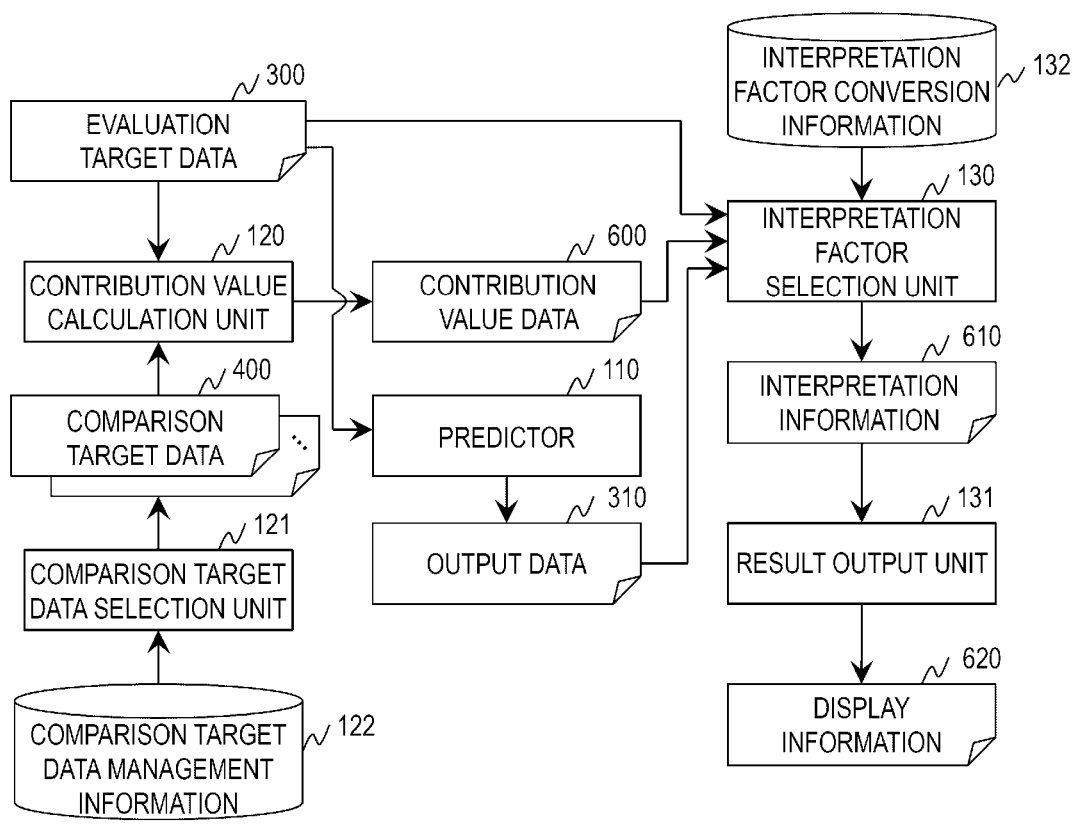
FIG. 6 shows a flow of processing of the computer system according to the first embodiment.
FIG. 7 shows an example of a data structure of contribution value data according to the first embodiment.
FIG. 8 shows an example of a data structure of interpretation information according to the first embodiment.
Figure 9A:
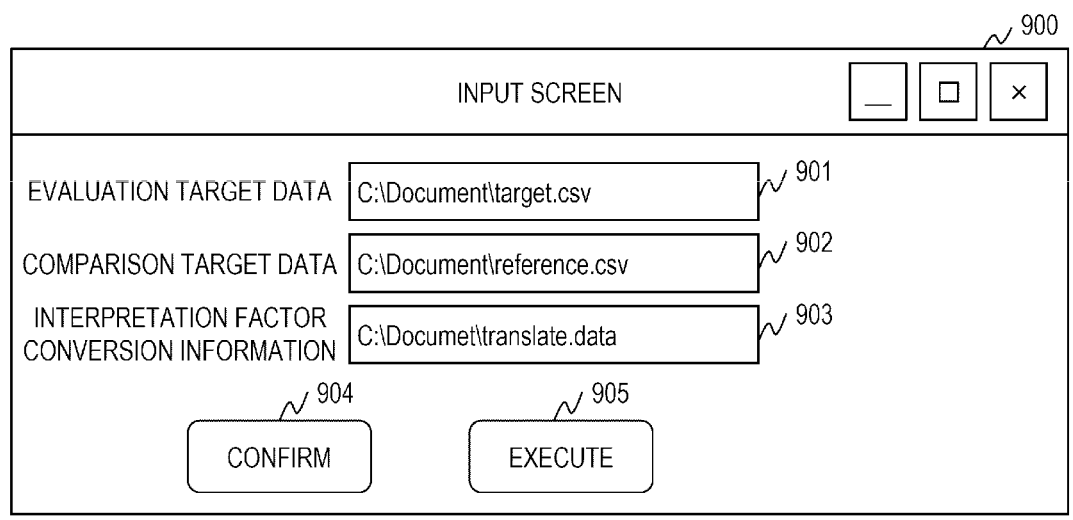
FIG. 9A shows an example of an input screen displayed on a terminal according to the first embodiment.
Figure 9B:
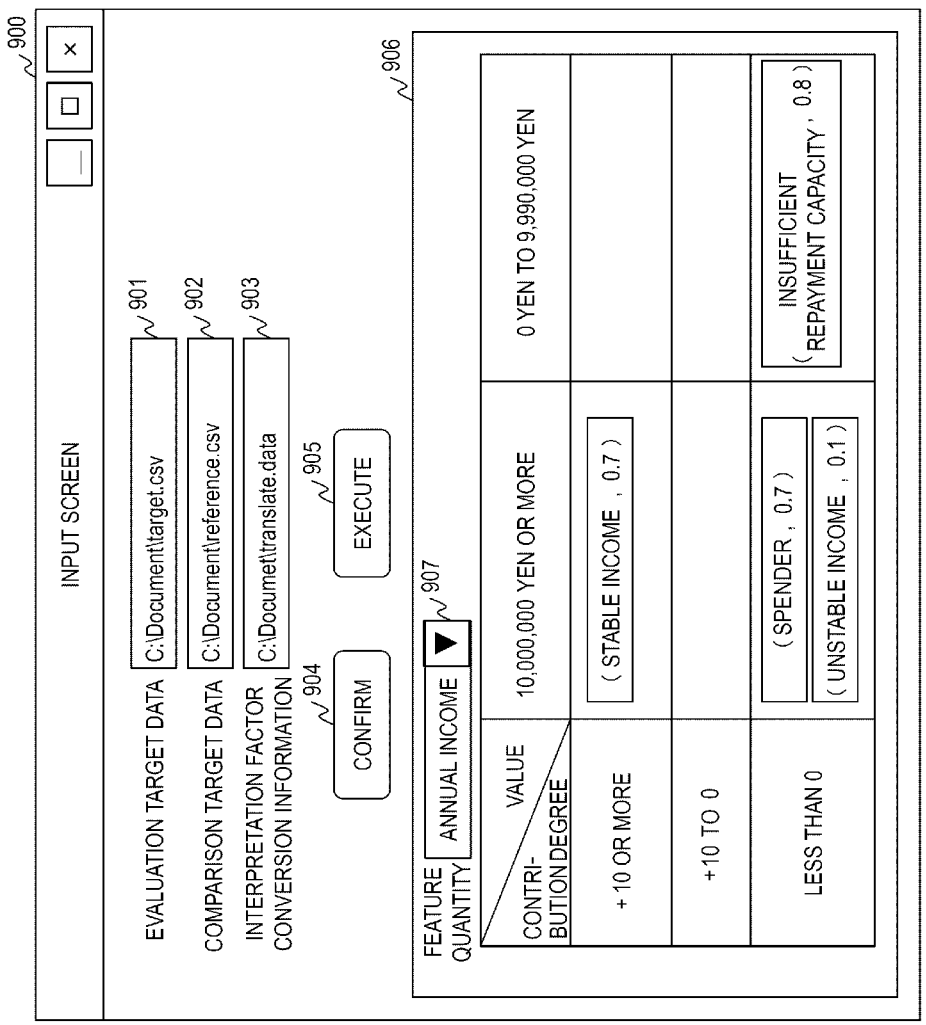
FIG. 9B shows an example of an input screen displayed on the terminal according to the first embodiment.

FIG. 6 shows a flow of processing of the computer system according to the first embodiment. Arrows in the drawing indicate the flow of data. FIG. 7 shows an example of a data structure of contribution value data 600 according to the first embodiment. FIG. 8 shows an example of a data structure of interpretation information 610 according to the first embodiment. FIGS. 9A and 9B shows an example of an input screen 900 displayed on the terminal 101 according to the first embodiment.

First, the data structures of the data and the information handled in the processing executed by the computer system will be described.

The contribution value data 600 includes an ID 701 and contribution values 702.

A field of the ID 701 stores identification information of the contribution value data 600. In the field of the ID 701, the same value as in the field of the ID 301 of the evaluation target data 300 is set.

A field group of the contribution value 702 stores the respective contribution values of the plurality of feature quantities contained in the evaluation target data 300. As will be described below, a contribution value is calculated using a known calculation method. The present invention is not limited to the calculation method of a contribution value.

The interpretation information 610 includes an entry including an interpretation factor 801 and a score 802. One entry corresponds to one interpretation factor.

A field of the interpretation factor 801 stores the interpretation factor specified based on the interpretation factor conversion information 132. A field of the score 802 stores a score.

Next, a flow of processing of the computer system will be described. First, the operation receiving unit presents the input screen 900 to the terminal 101. Here, the input screen 900 will be described.

The input screen 900 is a screen presented by the operation receiving unit, and is displayed on the terminal 101. The input screen 900 includes an evaluation target data setting field 901, a comparison target data setting field 902, an interpretation factor information setting field 903, a confirmation button 904, and an execute button 905.

The evaluation target data setting field 901 is a field for designating the evaluation target data 300. The comparison target data setting field 902 is a field for designating the comparison target data 400. The interpretation factor information setting field 903 is a field for designating the interpretation factor conversion information 132.

The confirmation button 904 is an operation button for confirming the conversion table 500 stored in the interpretation factor conversion information 132 specified in the interpretation factor information setting field 903. When the confirmation button 904 is operated, a conversion table confirmation field 906 is displayed on the input screen 900. The conversion table confirmation field 906 includes a feature quantity selection field 907.

The feature quantity selection field 907 is a field for selecting a feature quantity. A conversion table 500 corresponding to the feature quantity set in the feature quantity selection field 907 is displayed in the conversion table confirmation field 906.

Only a cell in which the interpretation factor data 510 is stored may be displayed in the conversion table confirmation field 906. It should be noted that all the conversion tables 500 may be displayed in the conversion table confirmation field 906. In this case, the conversion table confirmation field 906 does not include the feature quantity selection field 907.

The execution button 905 is a button for instructing generation of the interpretation information 610 of the evaluation target data 300. When the execution button 905 is operated, the terminal 101 transmits an interpretation information output request including information on the evaluation target data 300, the comparison target data 400, and the interpretation factor conversion information 132, which are designated by the user.

When the comparison target data 400 is generated from statistics such as the average value and the mode value of the evaluation target data 300 that was input in the past, or is randomly generated, the input screen 900 may not include the comparison target data setting field 902.

The input screen 900 has been described above. The description will now return to FIG. 6.

When receiving the interpretation information output request, the operation receiving unit outputs a calculation instruction of a predicted value to the computer 100-1, and outputs a calculation instruction of a contribution value of the evaluation target data 300 to the computer 100-2. The calculation instruction of a predicted value includes designation information of the evaluation target data 300, and the calculation instruction of a contribution value includes designation information of the comparison target data 400. The operation receiving unit outputs a generation instruction of the interpretation information 610 to the computer 100-3. The generation instruction of the interpretation information 610 includes designation information of the evaluation target data 300.

The predictor 110 of the computer 100-1 generates the output data 310 by processing the evaluation target data 300 based on the model information. The predictor 110 outputs the output data 310 to the computer 100-3.

The contribution value calculation unit 120 of the computer 100-2 transmits a selection instruction of the comparison target data 400 to the comparison target data selection unit 121. The selection instruction of the comparison target data 400 includes designation information of the comparison target data 400. When receiving the selection instruction of the comparison target data 400, the comparison target data selection unit 121 of the computer 100-2 acquires the comparison target data 400 to be used from the comparison target data management information 122 based on the designation information of the comparison target data 400. The comparison target data selection unit 121 outputs the comparison target data 400 acquired by the contribution value calculation unit 120.

When receiving the comparison target data 400, the contribution value calculation unit 120 calculates the contribution value of each feature quantity of the evaluation target data 300 based on the evaluation target data 300 and the comparison target data 400, and generates the contribution value data 600. The contribution value calculation unit 120 outputs the contribution value data 600 to the computer 100-3.

When receiving the output data 310, the contribution value data 600, and the generation instruction of the interpretation information 610, the interpretation factor selection unit 130 of the computer 100-3 generates the interpretation information 610, based on the evaluation target data 300 and the contribution value data 600, by referring to the conversion table 500 stored in the interpretation factor conversion information 132. The interpretation factor selection unit 130 outputs the evaluation target data 300, the output data 310, the contribution value data 600, and the interpretation information 610 to the result output unit 131.

The result output unit 131 of the computer 100-3 generates display information 620 for presenting the evaluation target data 300, the output data 310, the contribution value data 600, and the interpretation information 610 to the user. The result output unit 131 outputs the display information 620 to the operation receiving unit. The operation receiving unit transmits the display information 620 to the terminal 101.

In FIG. 6, the predicted value and the interpretation information 610 are presented in a series of processing. However, presentation of the predicted value and presentation of interpretation information 610 may be performed as separate processing. In this case, the input screen 900 may be divided into a field including an evaluation target data setting field 901, a comparison target data setting field 902, and an execution button for prediction, and a field including an interpretation factor information setting field 903, a confirmation button 904, and an execution button for interpretation.

Next, the processing executed in the computer system will be described in detail. First, the generation processing of the contribution value data 600 will be described.

Figure 10:
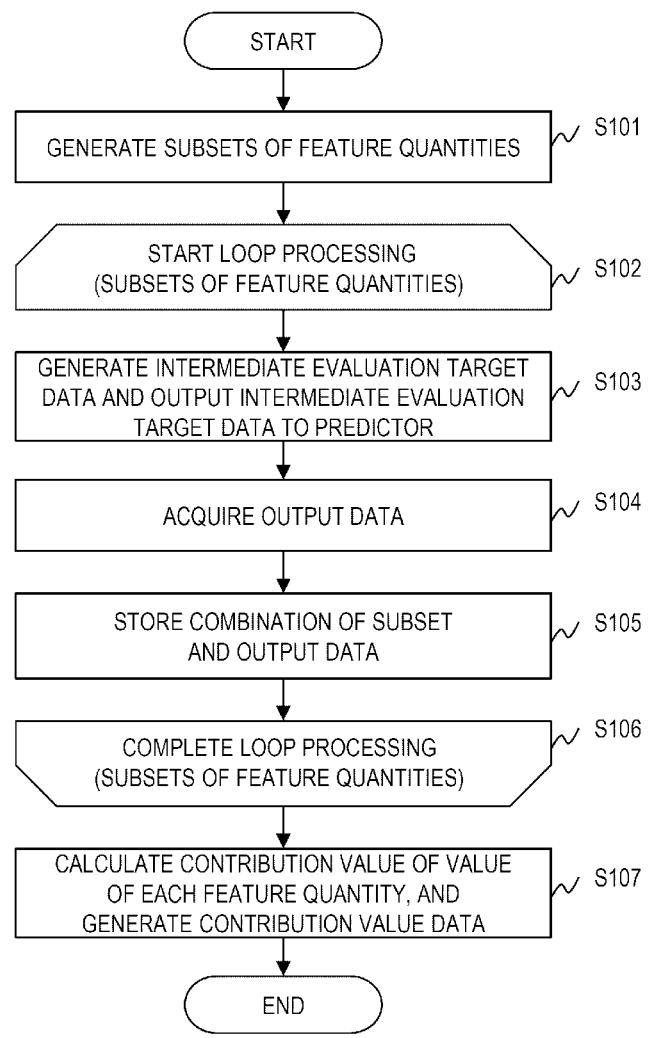
FIG. 10 is a flowchart showing an example of contribution value data generation processing executed by a contribution value calculation unit according to the first embodiment.

In the first embodiment, the contribution value is calculated using a calculation method described in Non-Patent Literature 1. Here, a summary of the calculation method of a contribution value will be described. FIG. 10 is a flowchart showing an example of contribution value data generation processing executed by the contribution value calculation unit 120 according to the first embodiment. FIGS. 11A, 11B, 11C, 11D, and 11E show an example of a data structure of the intermediate data 1100 according to the first embodiment.

The contribution value calculation unit 120 generates subsets of the feature quantities (step S101). It should be noted that the subset of the feature quantities includes an empty set as well.

Next, the contribution value calculation unit 120 starts loop processing of the subsets of feature quantities (step S102).

Specifically, the contribution value calculation unit 120 selects one subset from unprocessed subsets. The contribution value calculation unit 120 selects an empty set as an initial value.

Next, the contribution value calculation unit 120 generates the intermediate data 1100 based on the evaluation target data 300, the comparison target data 400, and a subset K, and outputs the generated intermediate data 1100 to the predictor 110 (step S103). The contribution value calculation unit 120 shifts to awaiting state until the output data 310 is output from the predictor 110.

Specifically, the contribution value calculation unit 120 generates the intermediate data 1100 by setting a value of a feature quantity of the evaluation target data 300 in the feature quantity contained in the subset, and setting a value of a feature quantity of the comparison target data 400 in the feature quantity not contained in the subset.

For example, when the evaluation target data 300-1 and the comparison target data 400 whose ID 401 is "1" is used, the intermediate data 1100 as shown in FIGS. 11A, 11B, 11C, 11D, and 11E is generated.

When the empty set is selected, intermediate data 1100-1 shown in FIG. 11A is generated. When a subset including the feature quantity "gender" as an element is selected, intermediate data 1100-2 shown in FIG. 11B is generated. When a subset including the feature quantity "age" as an element is selected, intermediate data 1100-3 shown in FIG. 11C is generated. When a subset including the feature quantities "gender" and "age" is selected, intermediate data 1100-4 shown in FIG. 11D is generated. When a subset including all the feature quantities as elements is selected, intermediate data 1100-5 shown in FIG. 11E is generated.

When receiving the intermediate data 1100, the predictor 110 generates the output data 310 by processing the intermediate data 1100 based on the model information. The predictor 110 outputs the output data 310 to the contribution value calculation unit 120.

The contribution value calculation unit 120 acquires the output data 310 output from the predictor 110 as intermediate output data (step S104), and stores the combination of the subset, the intermediate data 1100, and the intermediate output data in a work area (step S105).

Next, the contribution value calculation unit 120 determines whether the processing is completed for all subsets (step S106).

When it is determined that the processing is not completed for all the subsets, the contribution value calculation unit 120 returns to step S102 and selects a new subset.

When it is determined that the processing is completed for all the subsets, the contribution value calculation unit 120 calculates the contribution value of each feature quantity of the evaluation target data 300 by using the intermediate output data, and generates the contribution value data 600 from the calculated contribution value (step S107). Then, the contribution value calculation unit 120 terminates the contribution value data generation processing. Specifically, the following processing is executed.

(Processing A1) The contribution value calculation unit 120 selects a target feature quantity from the feature quantities contained in the evaluation target data 300.

(Processing A2) The contribution value calculation unit 120 multiplies a difference between the intermediate output data corresponding to a subset including the target feature quantity as an element and the intermediate output data corresponding to a subset not including the target feature quantity as an element by any weights for a combination of sets of feature quantities other than the target feature quantity, and adds up these values.

For example, a difference between the number of elements in the subset and the number of all the feature quantities can be used as a weight. A value which is obtained by dividing a value, obtained by multiplying a factorial of a value obtained by subtracting one from the number of elements in the subset by a factorial of the difference between the number of all the feature quantities and the number of elements in the subset, by a factorial of the number of all the feature quantities, can be used as a weight.

Figure 12:
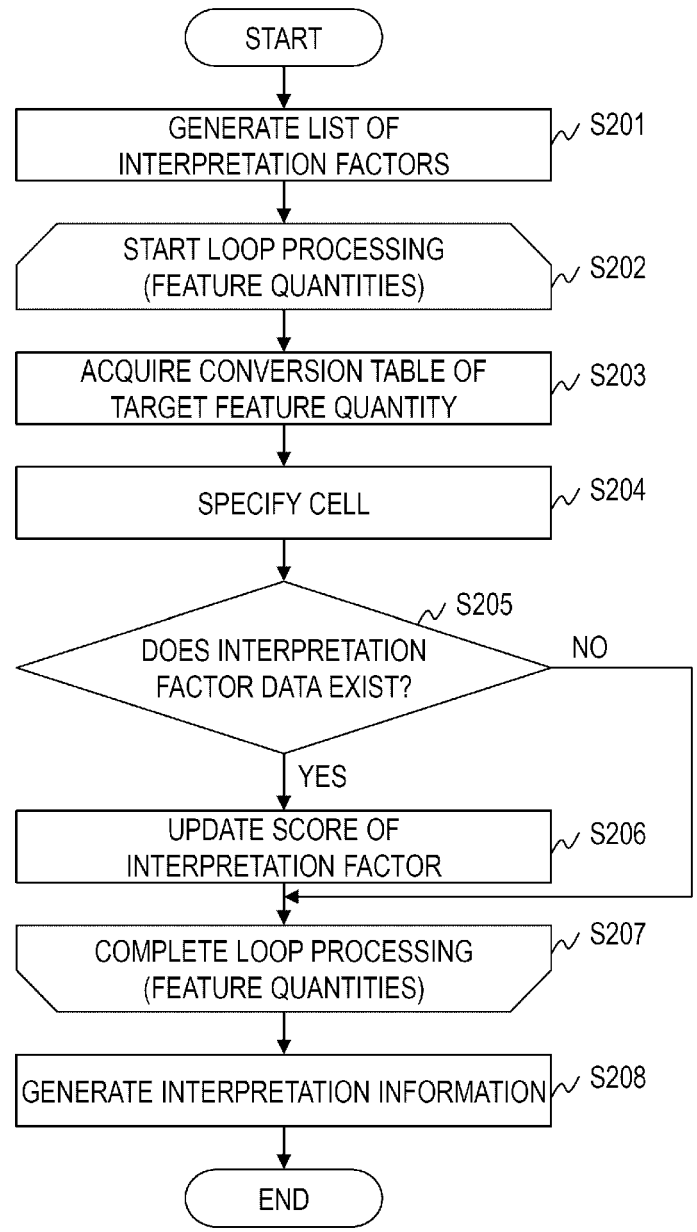
FIG. 12 is a flowchart showing an example of interpretation information generation processing executed by an interpretation factor selection unit according to the first embodiment.

FIG. 12 is a flowchart showing an example of interpretation information generation processing executed by the interpretation factor selection unit 130 according to the first embodiment.

The interpretation factor selection unit 130 generates a list of interpretation factors set in the interpretation factor conversion information 132 by referring to the interpretation factor conversion information 132 (step S201).

Specifically, in the interpretation factor conversion information 132, a list including an entry including an interpretation factor and a score is generated. Initial values of scores of all the interpretation factors are set as "0".

Next, the interpretation factor selection unit 130 starts loop processing of a feature quantity (step S202).

Specifically, the interpretation factor selection unit 130 selects one feature quantity from unprocessed feature quantities as a target feature quantity.

Next, the interpretation factor selection unit 130 acquires a conversion table 500 of the target feature quantity from the interpretation factor conversion information 132 (step S203).

Next, the interpretation factor selection unit 130 specifies a cell of the conversion table 500 based on a value and a contribution value of the target feature quantity contained in the evaluation target data 300 (step S204).

Specifically, the interpretation factor selection unit 130 specifies a column corresponding to an area including the value of the target feature quantity, and specifies a row corresponding to an area including the contribution value of the target feature quantity.

Next, the interpretation factor selection unit 130 determines whether the interpretation factor data 510 exists in the specified cell (step S205).

When it is determined that the interpretation factor data 510 does not exist in the specified cell, the interpretation factor selection unit 130 proceeds to step S207.

When it is determined that the interpretation factor data 510 exists in the specified cell, the interpretation factor selection unit 130 updates a score of an interpretation factor corresponding to the interpretation factor data 510 (step S206). Thereafter, the interpretation factor selection unit 130 proceeds to step S207.

Specifically, the interpretation factor selection unit 130 retrieves an entry corresponding to the interpretation factor 511 of the interpretation factor data 510 by referring to the list, and adds a value of the weight 512 to a score of the retrieved entry.

In step S207, the interpretation factor selection unit 130 determines whether the processing is completed for all the feature quantities (step S207).

When it is determined that the processing is not completed for all the feature quantities, the interpretation factor selection unit 130 returns to step S202 and selects a new feature quantity.

When it is determined that the processing is completed for all the feature quantities, the interpretation factor selection unit 130 generates the interpretation information 610 based on the list (step S208). Then, the interpretation factor selection unit 130 terminates the interpretation information generation processing.

For example, the interpretation factor selection unit 130 directly generates the list as the interpretation information 610. The interpretation factor selection unit 130 may select only an entry whose score is larger than a threshold, and generate the interpretation information 610 from the selected entry. The interpretation factor selection unit 130 may select any number of entries in descending order of the score, and generate the interpretation information 610 from the selected entry.

Figure 13:
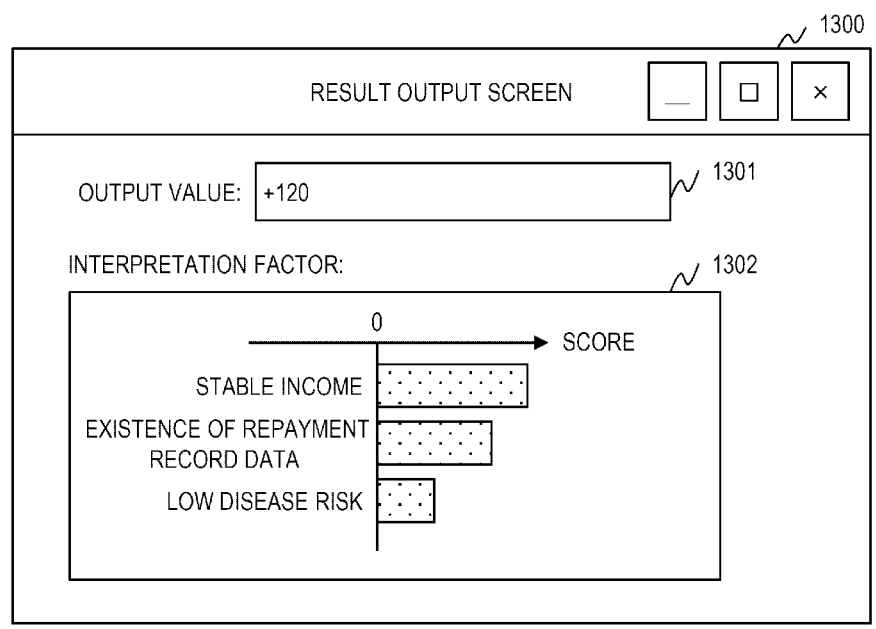
FIG. 13 shows an example of a result output screen displayed on the terminal according to the first embodiment.

FIG. 13 shows an example of a result output screen 1300 displayed on the terminal 101 according to the first embodiment.

The operation receiving unit presents the result output screen 1300 on the terminal 101 based on the display information 620. The result output screen 1300 includes a predicted value display field 1301 and an interpretation factor display field 1302.

The predicted value display field 1301 is a field for displaying a predicted value of the evaluation target data 300. The interpretation factor display field 1302 is a field for displaying an interpretation factor. In the interpretation factor display field 1302, the score 802 corresponding to the interpretation factor 801 of each entry of the interpretation information 610 is displayed as a bar graph.

The result output unit 131 may generate display information 620 for displaying, in the interpretation factor display field 1302, an entry whose value of the score 802 is larger than a threshold. The result output unit 131 may generate display information 620 for selecting any number of entries in descending order of the score 802 and displaying the selected entries in the interpretation factor display field 1302.

As described above, according to the first embodiment, the computer system can present the interpretation factor to the user as information useful for understanding the basis of the predicted value, together with the predicted value (prediction result) of the evaluation target data 300. The computer system can also present a score along with an interpretation factor.

The user can interpret the prediction basis with a certain degree of satisfaction by interpreting the abstraction about what characteristics and meaning the evaluation target data 300 has. In addition, the user can quantitatively evaluate the validity of each interpretation factor.

Second Embodiment

In the second embodiment, a method of generating the conversion table 500 will be described. Hereinafter, the second embodiment will be described focusing on differences from the first embodiment.

Figure 14:
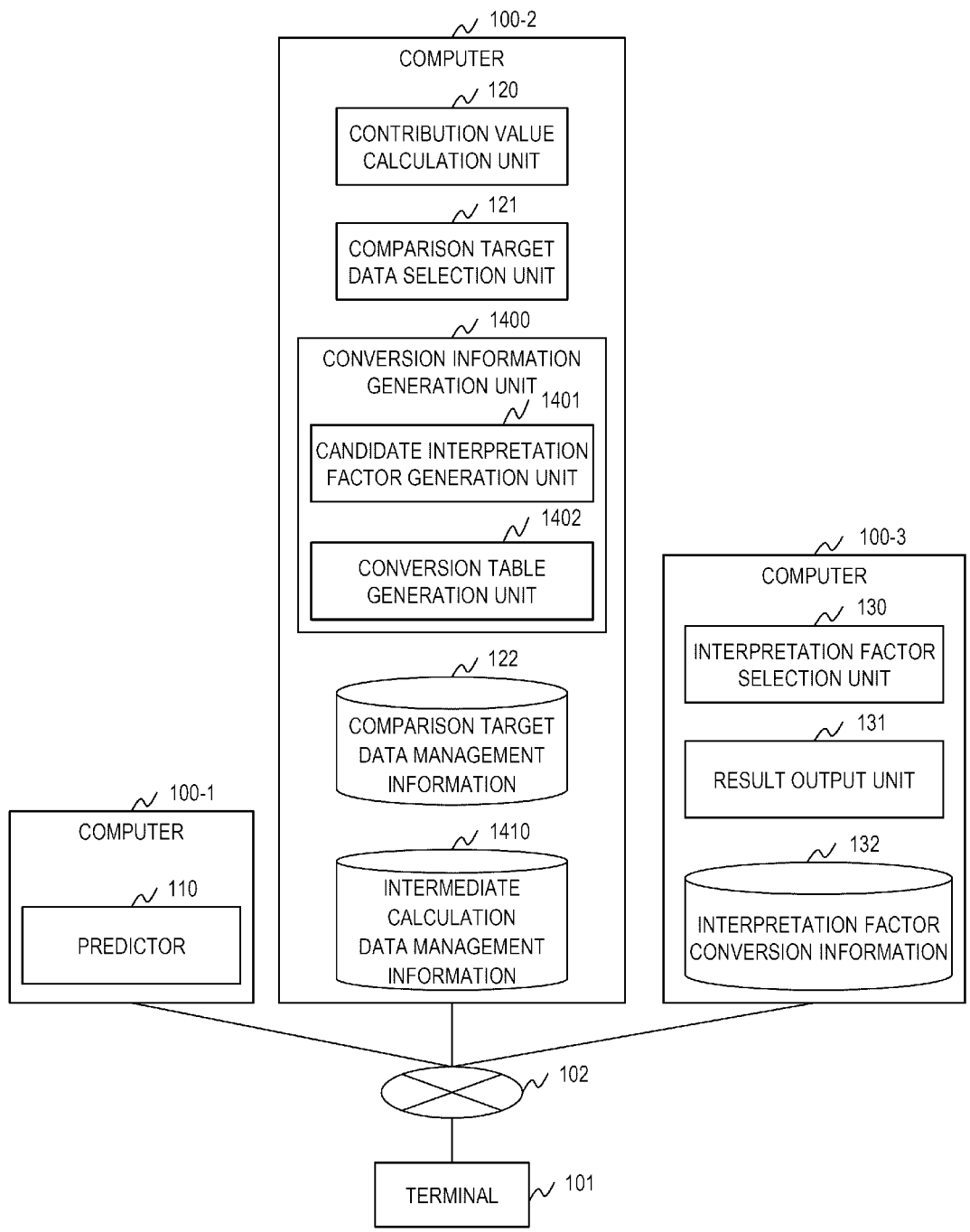
FIG. 14 shows a configuration example of a computer system according to a second embodiment.

FIG. 14 shows an example of a configuration of a computer system according to the second embodiment.

The configuration of the computer system according to the second embodiment is the same as that of the first embodiment. The hardware configuration of the computer 100 according to the second embodiment is the same as that of the first embodiment. The software configurations of the computers 100-1 and 100-3 according to the second embodiment are the same as those of the first embodiment. In the second embodiment, the software configuration of the computer 100-2 is different.

The computer 100-2 newly includes a conversion information generation unit 1400, and further stores intermediate calculation data management information 1410. The conversion information generation unit 1400 includes a candidate interpretation factor generation unit 1401 and a conversion table generation unit 1402.

Figure 15:
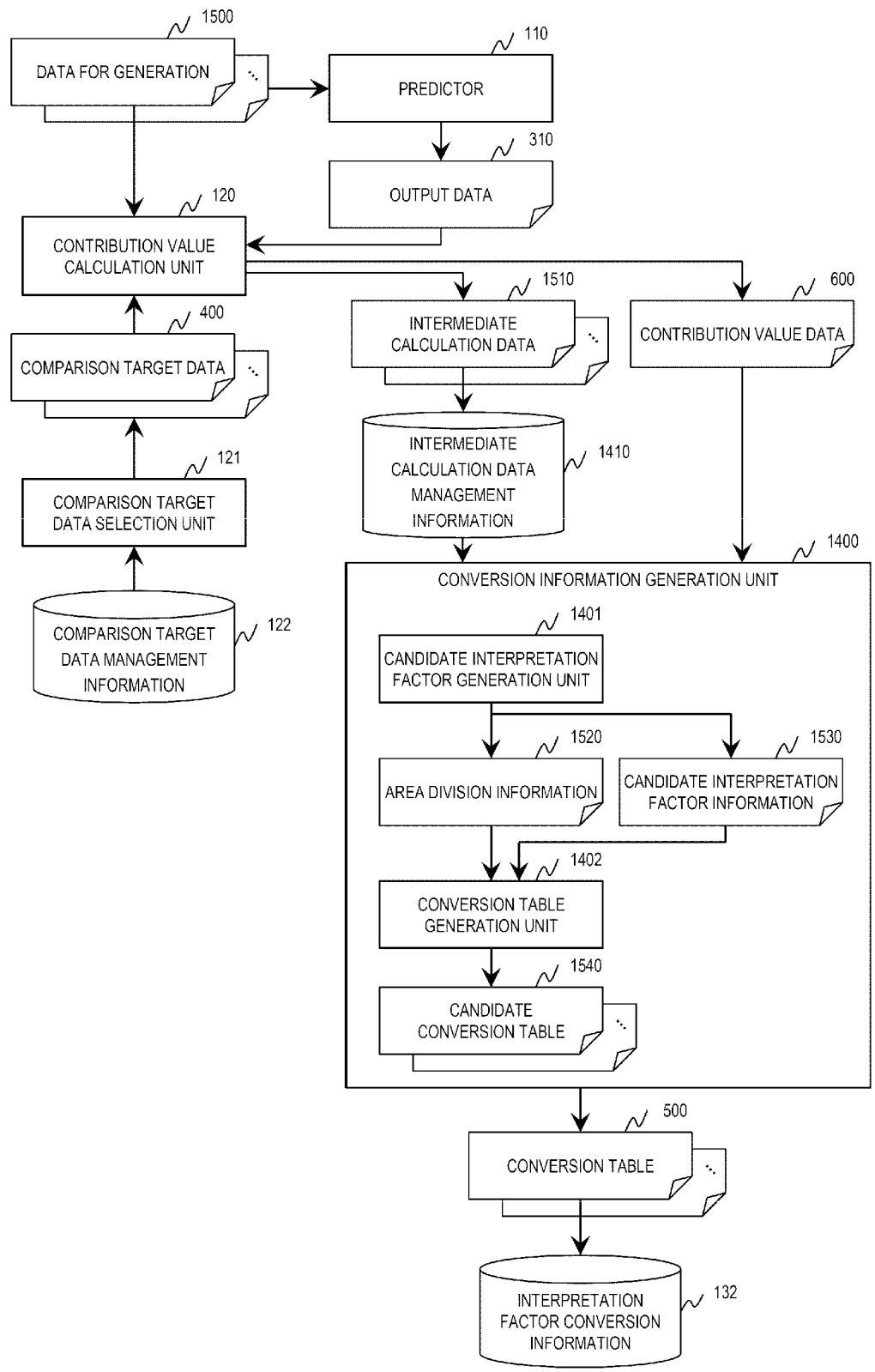
FIG. 15 shows a flow of processing of the computer system according to the second embodiment.
Figure 21:
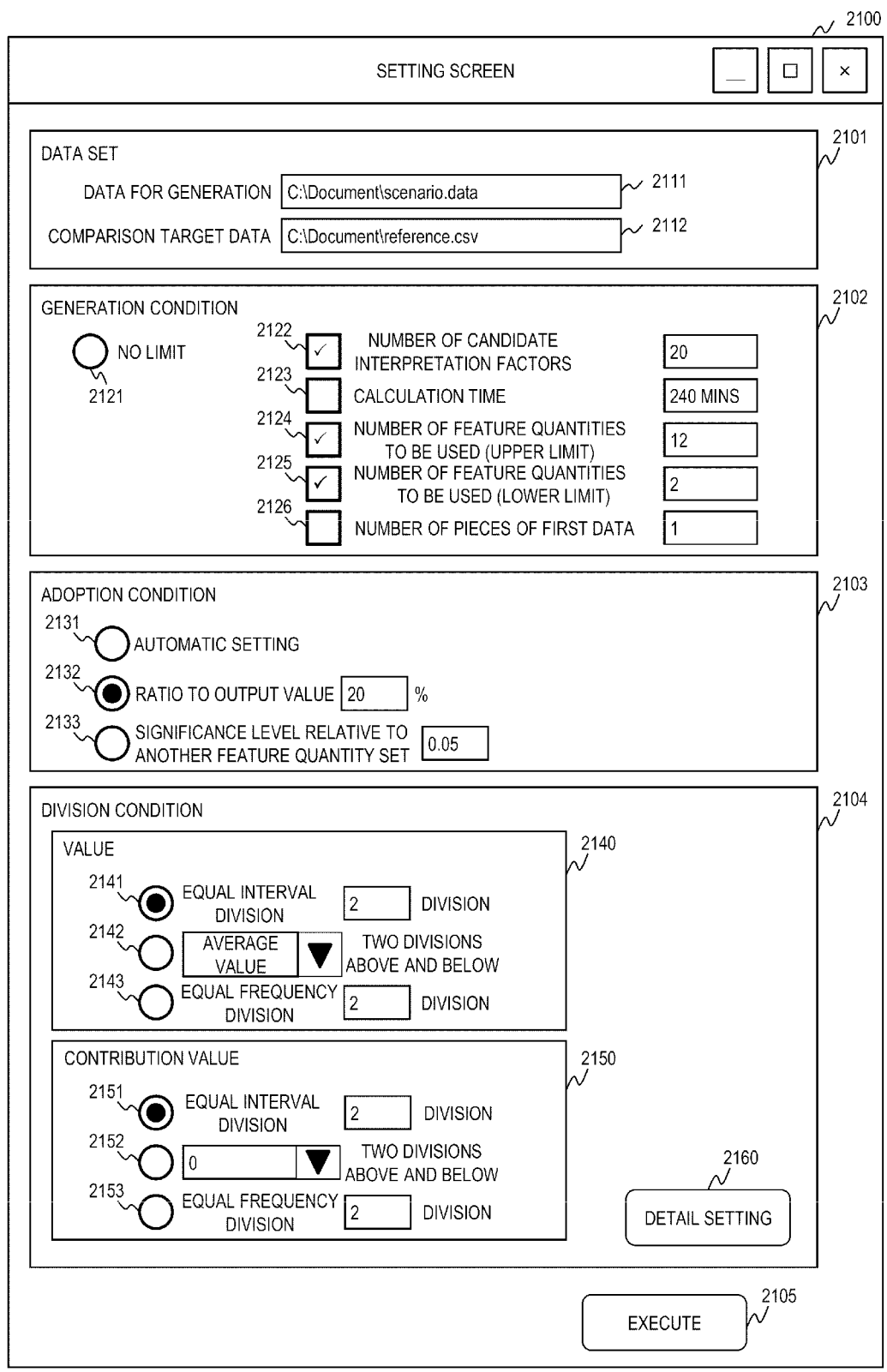
FIG. 21 shows an example of a setting screen displayed on a terminal according to the second embodiment.
Figure 22:
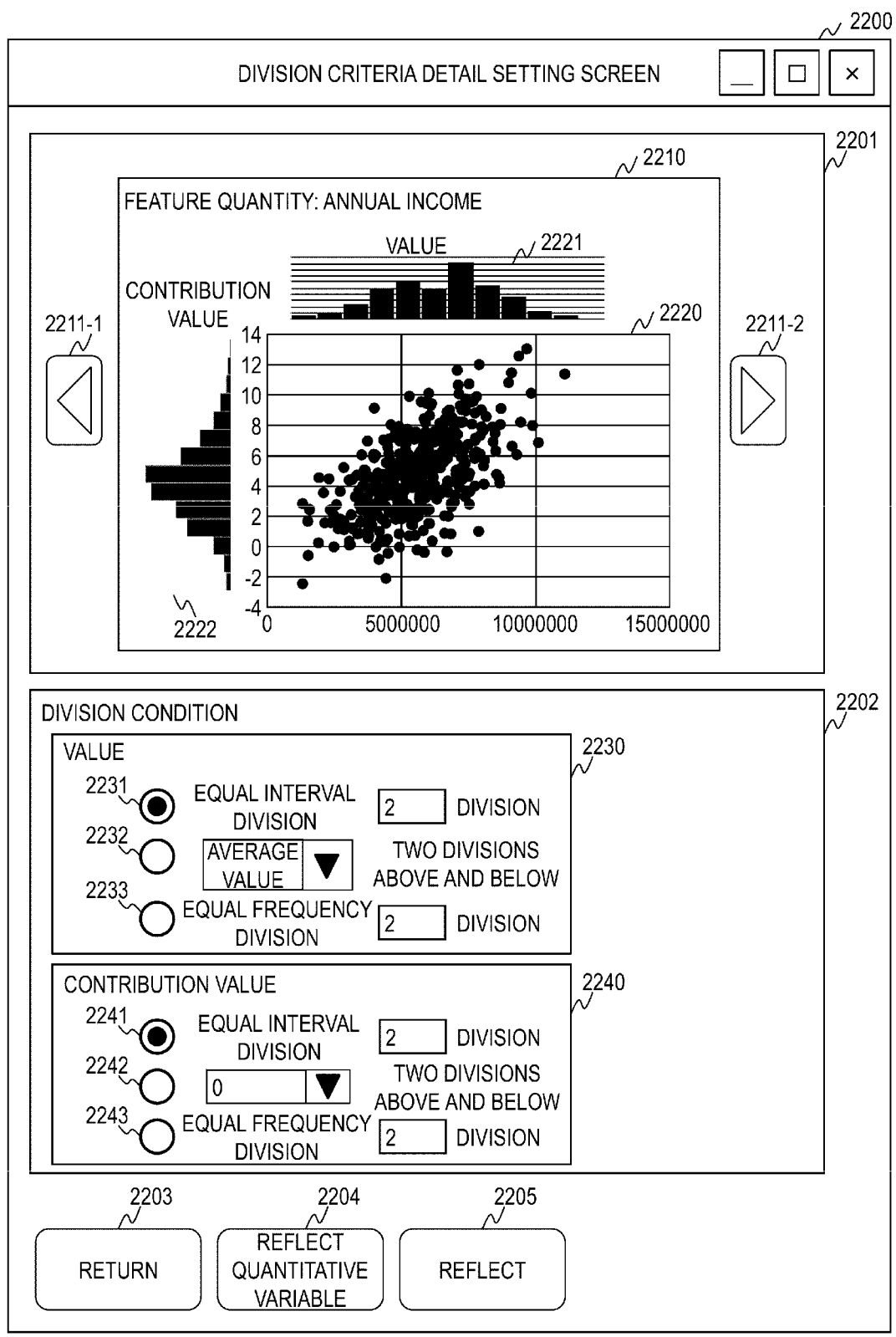
FIG. 22 shows an example of a division condition detail setting screen displayed on the terminal according to the second embodiment.
Figure 23:
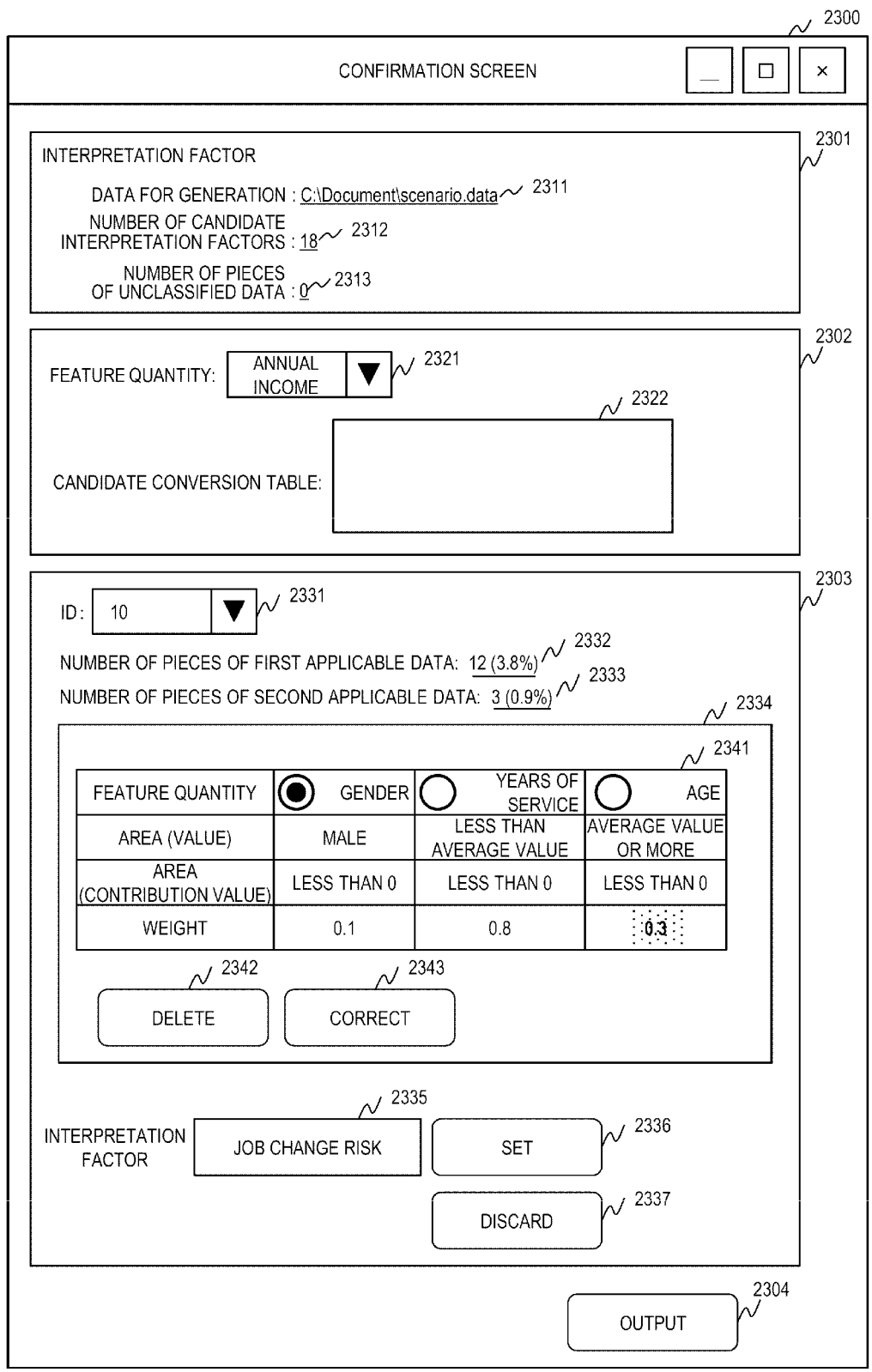
FIG. 23 shows an example of a confirmation screen displayed on the terminal according to the second embodiment.

FIG. 15 shows a flow of processing of the computer system according to the second embodiment. Arrows in the figure indicate the flow of data. FIG. 16 shows an example of a data structure of the data for generation 1500 according to the second embodiment. FIG. 17 shows an example of a data structure of intermediate calculation data 1510 according to the second embodiment. FIG. 18 shows an example of a data structure of area division information 1520 according to the second embodiment. FIG. 19 shows an example of a data structure of candidate interpretation factor information 1530 according to the second embodiment. FIG. 20 shows an example of a data structure of a candidate conversion table 1540 according to the second embodiment. FIG. 21 shows an example of a setting screen 2100 displayed on the terminal 101 according to the second embodiment. FIG. 22 shows an example of a division condition detail setting screen 2200 displayed on the terminal 101 according to the second embodiment. FIG. 23 shows an example of a confirmation screen 2300 displayed on the terminal 101 according to the second embodiment.

First, the data structures of the data and the information handled in the processing executed by the computer system will be described.

The data for generation 1500 has the same data structure as the evaluation target data 300, and includes an ID 1601 and feature quantities 1602. A field of the ID 1601 stores identification information of the data for generation 1500. In the field of the ID 1601 according to the second embodiment, a number is stored. A field of the feature quantity 1602 is the same as the field of the feature quantity 302.

The intermediate calculation data 1510 includes an ID 1701, a reference ID 1702, a subset 1703, feature quantities 1704, and an output value 1705.

A field of the ID 1701 stores identification information of the intermediate calculation data 1510. It is assumed that the same identification information as the intermediate data 1100 is set in the ID 1701. In the present embodiment, the intermediate data 1100 is generated based on the data for generation 1500 and the comparison target data 400.

A field of the reference ID 1702 stores identification information of the data for generation 1500 used at the time of generating the intermediate data 1100. The field of the reference ID 1702 stores the same value as that of the ID 1601.

A field of the subset 1703 stores a combination of feature quantities of the data for generation 1500 whose values were set at the time of generating the intermediate data 1100. When the field of the subset 1703 is empty, the intermediate data 1100 matches the comparison target data 400. On the other hand, when all the feature quantities are set in the subset 1703, the intermediate data 1100 matches the data for generation 1500.

A field group of the feature quantity 1704 stores values of feature quantities constituting the intermediate data 1100. A field of the output value 1705 stores a value output by the predictor 110 to which the intermediate data 1100 is input.

The area division information 1520 stores entries each including a feature quantity 1801, a division area (value) 1802, and a division area (contribution value) 1803. One entry corresponds to one feature quantity.

A field of the feature quantity 1801 stores identification information of a feature quantity. The feature quantity 1801 is also used as identification information of an entry.

A field of the division area (value) 1802 stores information on an area generated by dividing a value range of the value of the feature quantity. In the field of division area (value) 1802, data in which identification information of the area is associated with a range of the value or a type of the value is stored as many as the number of areas.

A field of the division area (contribution value) 1803 stores information on an area generated by dividing a value range of the contribution value of the feature quantity. In the field of the division area (contribution value) 1803, data in which identification information of the area is associated with a range of the contribution value is stored as many as the number of areas.

The candidate interpretation factor information 1530 stores entries each including an ID 1901, a feature quantity 1902, an area (value) 1903, an area (contribution value) 1904, a weight 1905, the number of pieces of first data 1906, the number of pieces of second data 1907, an interaction value 1908, and an interpretation factor 1909. One entry corresponds to one candidate interpretation factor.

A field of the ID 1901 stores identification information of a candidate interpretation factor. The field of the ID 1901 corresponds to an interpretation factor ID 2001.

A field of the feature quantity 1902, a field of the area (value) 1903, and a field of the area (contribution value) 1904 stores information indicating classification criteria of the candidate interpretation factors.

The field of the feature quantity 1902 stores identification information of a feature quantity serving as a classification criterion of the candidate interpretation factors. One or more feature quantities are set in one entry.

The field of the area (value) 1903 stores an area of a value of a feature quantity corresponding to the feature quantity 1902. The field of the area (contribution value) 1904 stores an area of a contribution value of a feature quantity corresponding to the feature quantity 1902.

The data for generation 1500, in which a value of a feature quantity corresponding to the feature quantity 1902 is contained in the area (value) 1903, and a contribution value of a feature quantity corresponding to the feature quantity 1902 is contained in the area (contribution value) 1904, is classified as data corresponding to the candidate interpretation factor corresponding to the entry.

A field of the weight 1905 stores a weight that is a value representing the degree of the validity corresponding to the candidate interpretation factor. When the weight is not taken into consideration, the field of the weight 1905 may not be contained.

A field of the number of pieces of the first data 1906 stores the number of pieces of data for generation 1500 satisfying the classification criteria set in the entry, that is, the number of pieces of data for generation 1500 corresponding to the candidate interpretation factor corresponding to the entry. The field of the number of pieces of the first data 1906 may store a ratio of the number of pieces of the data for generation 1500 corresponding to the candidate interpretation factor relative to the total number of pieces of the data for generation 1500.

A field of the number of pieces of the second data 1907 stores the number of pieces of data for generation 1500 corresponding only to the candidate interpretation factor corresponding to the entry. The field of the number of pieces of the second data 1907 may store a ratio of the number of pieces of the data for generation 1500 corresponding only to the candidate interpretation factor relative to the total number of pieces of the data for generation 1500.

A field of the interaction value 1908 stores an interaction value of a set of the feature quantities 1902 in the data for generation 1500 corresponding to the candidate interpretation factor. In the field of the interaction value 1908, a combination of the identification information of the data for generation 1500 and the interaction value is stored as many as the number of pieces of the first data.

Here, the interaction value (second evaluation value) is a value that represents magnitude of contribution of the set of values of feature quantities and that corresponds to the output value of the data for generation 1500. The interaction values can be calculated by using methods described in Lundberg, Scott M., Gabriel G. Erion, and Su-In Lee. "Consistent Individualized Feature Attribution for Tree Ensembles." ArXiv preprint arXiv: 1802.03888 (2018) (Non-Patent Literature 2) and Grabisch, Michel. "K-order additive discrete fuzzy measures and their representation." Fuzzy sets and systems 92.2 (1997): 167-189. (Non-Patent Literature 3). A value, which indicates what kind of feature quantity the data for generation 1500 has as compared with the comparison target data 400 and how much the fact contributes to the output value, is calculated as an interaction value.

A field of the interpretation factor 1909 stores an interpretation factor (natural language information) set for the candidate interpretation factor. At a time point when the candidate interpretation factor information 1530 is generated, the field of the interpretation factor 1909 of each entry is blank. The setting of the value to the field of the interpretation factor 1909 is performed by the user.

The candidate conversion table 1540 has the same data format as the conversion table 500. Candidate interpretation factor data 2000 is stored in at least one cell of the candidate conversion table 1540. Two or more pieces of candidate interpretation factor data 2000 may be stored in a cell.

The candidate interpretation factor data 2000 includes an interpretation factor ID 2001 and a weight 2002. The interpretation factor ID 2001 is identification information of the candidate interpretation factor. The weight 2002 is the same as the weight 512.

Next, a flow of processing of the computer system will be described. First, the operation receiving unit presents the setting screen 2100 to the terminal 101. Here, the setting screen 2100 and the division condition detail setting screen 2200 will be described.

The setting screen 2100 is a screen presented by the operation receiving unit, and is displayed on the terminal 101. The setting screen 2100 includes a data set setting field 2101, a generation condition setting field 2102, an adoption condition setting field 2103, a division condition setting field 2104, and an execution button 2105.

The data set setting field 2101 is a field for designating data to be used for processing. A value set in the data set setting field 2101 is output as data set information. The data set setting field 2101 includes a data for generation setting field 2111 and a comparison target data setting field 2112.

The data for generation setting field 2111 is a field for designating the data for generation 1500 to be used. The comparison target data setting field 2112 is a field for designating the comparison target data 400.

When the comparison target data 400 is generated from statistics such as the average value and the mode value of the evaluation target data 300 that was input in the past, or is randomly generated, the comparison target data setting field 2112 may not be contained.

The generation condition setting field 2102 is a field for setting a generation condition that defines constraints on generation of candidate interpretation factors. The values set in the generation condition setting field 2102 are output as generation condition information. The generation condition setting field 2102 includes a radio button 2121 and check fields 2122, 2123, 2124, 2125, and 2126.

The radio button 2121 is a button that is selected when the generation condition is not set. In this case, inputs to the check fields 2122, 2123, 2124, 2125, and 2126 are invalidated.

The check field 2122 is a field to be operated to set an upper limit value of the number of the candidate interpretation factors. The user operates the check field 2122 to set a value equal to or larger than 1.

The check field 2123 is a field to be operated to set an upper limit value of calculation time of the processing of generating the conversion table 500. The user operates the check field 2123 to set a value equal to or larger than 0. The upper limit value of the calculation time may be set for specific processing.

The check field 2124 is a field to be operated to set an upper limit value of the number of feature quantities to be contained as a classification criterion for one interpretation factor. The user operates the check field 2124 to set a value equal to or larger than 1.

The check field 2125 is a field to be operated to set a lower limit value of the number of feature quantities to be contained as a classification criterion for one interpretation factor. The user operates the check field 2125 to set a value equal to or larger than 1.

The check field 2126 is a field to be operated to set a lower limit value of the number of the data for generation 1500 corresponding to the candidate interpretation factor. The user operates the check field 2126 to set a value equal to or larger than 1.

The adoption condition setting field 2103 is a field for setting an adoption condition of the interpretation factor based on an interaction value. A value set in the adoption condition setting field 2103 is output as adoption condition information. The adoption condition setting field 2103 includes radio buttons 2131, 2132 and 2133.

The radio button 2131 is a radio button operated to use a preset adoption condition. In the present embodiment, the candidate interpretation factors are determined in descending order of the interaction values within a range that satisfies the generation condition.

The radio button 2132 is a radio button operated to use the adoption condition based on a ratio between the interaction value and the predicted value. The user operates the radio button 2132 to set a value equal to or larger than 0.

The radio button 2133 is a radio button operated to use the adoption condition based on a significance level. The user operates the radio button 2133 to set a value larger than 0 and smaller than 1. A value used in other hypothesis test methods, such as a p value, may be set in the radio button 2133.

The division condition setting field 2104 is a field for setting division conditions for the value ranges of the value and the contribution value of the feature quantity. The value set in the division condition setting field 2104 is output as the division condition information. The division condition setting field 2104 includes a value division condition field 2140, a contribution value division condition field 2150, and a detail setting button 2160.

The value division condition field 2140 is a field for setting the division condition of the value range of the value of the feature quantity, and includes radio buttons 2141, 2142, and 2143.

The radio button 2141 is a radio button operated to equally divide the value range of the value. The user operates the radio button 2141 to set a value equal to or larger than 1 as the number of divisions.

The radio button 2142 is a radio button operated to equally divide the value range of the value into two parts based on statistics such as a median value, an average value, and a mode value. The user operates the radio button 2142 to set a reference statistic. It should be noted that different values may be set for the feature quantity depending on the difference of a quantitative variable or a categorical variable.

The radio button 2143 is a radio button operated to equally divide the value range of the value based on the number of pieces of the data for generation 1500 contained in the area. The user operates the radio button 2143 to set a value equal to or larger than 1 as the number of divisions.

The contribution value division condition field 2150 is a field for setting the division condition of the value range of the contribution value of the feature quantity, and includes radio buttons 2151, 2152, and 2153. The radio buttons 2151, 2152, and 2153 are similar to the radio buttons 2141, 2142, and 2143.

The detail setting button 2160 is a button operated to set a division condition for each feature quantity. When the user operates the detail setting button 2160, the division condition detail setting screen 2200 is displayed. Details of the division condition detail setting screen 2200 will be described below.

When the division condition information is preset, the division condition setting field 2104 may not be contained in the setting screen 2100. The value division condition field 2140 may be provided with radio buttons for automatically setting a division condition corresponding to anyone of the radio buttons 2141, 2142, and 2143.

The execution button 2105 is a button for instructing generation of the conversion table 500. When the execution button 2105 is operated, the terminal 101 transmits a generation request of the conversion table 500 that includes data set information, generation condition information, adoption condition information, and division condition information.

The setting screen 2100 may include an operation button for registering, in the computer 100-2, a value of each field as initial condition information. The setting screen 2100 may include an operation button for initializing the value of each field.

The setting screen 2100 has been described above. Next, the division condition detail setting screen 2200 will be described.

The division condition detail setting screen 2200 includes a feature quantity confirmation field 2201, a division condition setting field 2202, a return button 2203, a quantitative variable reflection button 2204, and a reflection button 2205.

The feature quantity confirmation field 2201 is a field for displaying information on the feature quantity of the data for generation 1500. The feature quantity confirmation field 2201 includes a display field 2210 and a selection button 2211.

The display field 2210 is a field for displaying information on distribution of the data for generation 1500 related to a certain feature quantity. A distribution graph 2220 is displayed in the display field 2210 according to the present embodiment.

The distribution graph 2220 is a graph such as a scatter graph or a heat map which shows the distribution of the data for generation 1500 with the value and the contribution value of the feature quantity as axes.

A value histogram 2221 is a histogram showing the number of pieces of the data for generation 1500 classified into categories of the value of the feature quantity. The categories are set at any width. A contribution value histogram 2222 is a histogram showing the number of pieces of the data for generation 1500 belonging to the categories of the contribution value of the feature quantity. The categories are set at any width.

The user can set the division conditions of the value ranges of the value and the contribution value of the feature quantity by referring to the information in the display field 2210.

The selection button 2211 is an operation button for changing the feature quantity to be displayed in the display field 2210. When a selection button 2211-1 is operated, information on a previous feature quantity of a current feature quantity is displayed in the display field 2210, and when a selection button 2211-2 is operated, information on a next feature quantity of the current feature quantity is displayed in the display field 2210.

The feature quantity confirmation field 2201 may include a field for directly designating a feature quantity instead of the selection button 2211. The feature quantity confirmation field 2201 may include a field for selecting feature quantities having a certain relation based on the value of the feature quantity, instead of the selection button 2211. When information of all the feature quantities can be displayed in the feature quantity confirmation field 2201, the selection button 2211 may not be contained in the feature quantity confirmation field 2201.

The division condition setting field 2202 is a field for setting division conditions of the value ranges of the value and the contribution value of the feature quantity. The division condition setting field 2202 includes a value division condition field 2230 and a contribution value division condition field 2240.

The value division condition column 2230 is a field for setting the division condition of the value range of the value of the feature quantity, and includes radio buttons 2231, 2232, and 2233. The radio buttons 2231, 2232, and 2233 are the same as the radio buttons 2141, 2142, and 2143.

The contribution value division condition field 2240 is a field for setting the division condition of the value range of the contribution value of the feature quantity, and includes radio buttons 2241, 2242, and 2243. The radio buttons 2241, 2242, and 2243 are the same as the radio buttons 2151, 2152, and 2153.

A return button 2203 is an operation button for switching a display from the division condition detail setting screen 2200 to the setting screen 2100. When the return button 2203 is operated, the value set using the division condition detail setting screen 2200 is output as the division condition information.

The quantitative variable reflect button 2204 is an operation button for setting the value set in the division condition setting field 2202 as a division condition of all the feature quantities corresponding to the quantitative variable. The division condition detail setting screen 2200 may include a categorical variable reflect button instead of the quantitative variable reflect button 2204.

The reflect button 2205 is an operation button for setting the value set in the division condition setting field 2202 as the division condition of all the feature quantities.

The division condition detail setting screen 2200 may include an operation button for storing, in the computer 100-2, the division condition information set via the division condition detail setting screen 2200, and an operation button for instructing discarding or initialization of the division condition information. The description will be returned to FIG. 15.

When receiving the generation request of the conversion table 500, the operation reception unit outputs a calculation instruction of the predicted value to the computer 100-1, and outputs the generation request of the conversion table 500 to the computer 100-2. The calculation instruction of the predicted value includes designation information of the data for generation 1500.

The predictor 110 of the computer 100-1 generates the output data 310 by processing the data for generation 1500 based on the model information. The predictor 110 outputs the output data 310 to the computer 100-2.

When receiving the generation request of the conversion table 500, the contribution value calculation unit 120 of the computer 100-2 transmits a selection instruction of the comparison target data 400 to the comparison target data selection unit 121. The selection instruction of the comparison target data 400 includes designation information of the comparison target data 400. When receiving the selection instruction of the comparison target data 400, the comparison target data selection unit 121 acquires the comparison target data 400 to be used from the comparison target data management information 122, based on the designation information of the comparison target data 400. The comparison target data selection unit 121 outputs the comparison target data 400 acquired by the contribution value calculation unit 120.

When receiving the comparison target data 400, the contribution value calculation unit 120 generates the contribution value data 600 based on the data for generation 1500 and the comparison target data 400. One piece of contribution value data 600 is generated for one piece of data for generation 1500. A method of generating the contribution value data 600 is the same as that of the first embodiment, and a description thereof will be omitted.

In addition, the contribution value calculation unit 120 stores, in the intermediate calculation data management information 1410, the intermediate data 1100 generated when the contribution value data 600 for the data for generation 1500 is calculated, identification information of the data for generation 1500, and intermediate calculation data 1510 including the subset and the intermediate output data.

When receiving the output data 310 of the data for generation 1500, the contribution value calculation unit 120 outputs a generation instruction of the conversion table 500 to the conversion information generation unit 1400. The generation instruction includes output data 310, the contribution value data 600, the generation condition information, the adoption condition information, and the division condition information.

The candidate interpretation factor generation unit 1401 of the conversion information generation unit 1400 generates the area division information 1520 and the candidate interpretation factor information 1530 based on the output data 310, the contribution value data 600, the intermediate calculation data 1510, the generation condition information, the adoption condition information, and the division condition information. The candidate interpretation factor generation unit 1401 outputs a selection instruction to the conversion table generation unit 1402.

When the conversion table generation unit 1402 receives the selection instruction, the conversion table generation unit 1402 of the conversion information generation unit 1400 generates the candidate conversion table 1540 based on the area division information 1520 and the candidate interpretation factor information 1530, generates display information for presenting the candidate conversion table 1540 and the like, and outputs the display information to the operation receiving unit. The operation receiving unit transmits the display information to the terminal 101.

The terminal 101 displays the confirmation screen 2300 based on the display information generated by the conversion table generation unit 1402. Here, the confirmation screen 2300 will be described.

The confirmation screen 2300 is a screen presented by the operation receiving unit, and is displayed on the terminal 101. The confirmation screen 2300 includes an interpretation factor information display field 2301, a conversion table display field 2302, a candidate interpretation factor display field 2303, and an Output Button 2304.

The interpretation factor information display field 2301 is a field for displaying a summary of the candidate interpretation factor, and includes a data for generation display field 2311, a candidate interpretation factor number field 2312, and an unclassified data number field 2313.

The data for generation display field 2311 displays a file or the like for storing the data for generation 1500 to be used. The candidate interpretation factor number field 2312 displays the number of generated candidate interpretation factors. The unclassified data number field 2313 displays the number of pieces of data for generation 1500 not classified as any of the generated candidate interpretation factors.

The conversion table display field 2302 displays a candidate conversion table 1540, and includes a feature quantity selection field 2321 and a candidate conversion table display field 2322.

The feature quantity selection field 2321 is a field for selecting a feature quantity. The candidate conversion table display field 2322 displays the candidate conversion table 1540 corresponding to the feature quantity set in the feature quantity selection field 2321.

The conversion table display field 2302 may include an operation button such as a selection button 2211, instead of the feature quantity selection field 2321. When all the candidate conversion tables 1540 can be displayed in the conversion table display field 2302, the feature quantity selection field 2321 may not be contained in the feature quantity confirmation field 2201.

The candidate interpretation factor display field 2303 displays detailed information of the candidate interpretation factor, and includes an ID selection field 2331, a first corresponding data number field 2332, a second corresponding data number field 2333, a classification condition confirmation field 2334, an interpretation factor setting field 2335, a setting button 2336, and a discarding button 2337.

The ID selection field 2331 is a field for selecting a candidate interpretation factor. As will be described below, a value corresponding to the ID 1901 is displayed in the candidate interpretation factor.

Information of the entries of the candidate interpretation factor information 1530 corresponding to the ID selection field 2331 is displayed in the first applicable data number field 2332, the second applicable data number field 2333, and the classification condition confirmation field 2334.

The first applicable data number field 2332 displays a value stored in the first data number field 1906. The second applicable data number field 2333 displays a value stored in the second data number field 1907.

The classification condition confirmation field 2334 is a field for displaying information of a feature quantity that is a classification condition of the candidate interpretation factor, and includes feature quantity information 2341, a Delete Button 2342, and a Correct Button 2343.

The feature quantity information 2341 is data in a format of a table in which entries each formed of four fields of a feature quantity, a value area, a contribution value area, and a weight are arranged in a column direction. One column corresponds to a row of a feature quantity contained in the entry of the candidate interpretation factor information 1530.

The field of the feature quantity includes a radio button. Any value can be set by the user in the field of the weight.

The candidate interpretation factor display field 2303 may include an operation button like the selection button 2211, instead of the ID selection field 2331. When information of all candidate interpretation factors can be displayed in the candidate interpretation factor display field 2303, the ID selection field 2331 may not be contained in the candidate interpretation factor display field 2303.

The Delete Button 2342 is an operation button for deleting an entry in which the radio button of the field of the feature quantity is operated. When the Delete Button 2342 is operated, the terminal 101 transmits a deletion request including the identification information of the candidate interpretation factor and the identification information of the feature quantity which are designated by the user. In this case, the conversion table generation unit 1402 deletes the row of the feature quantity selected from the entries of the candidate interpretation factor information 1530.

The Correct Button 2343 is an operation button for reflecting a user input. When the Correct Button 2343 is operated, the terminal 101 transmits a modification request including the identification information of the candidate interpretation factor, the identification information of the feature quantity, and the value of the weight, which are designated by the user. In this case, the conversion table generation unit 1402 updates the value of the weight 1905 of the candidate interpretation factor information 1530 based on a correct content.

The interpretation factor setting field 2335 is a field for setting an interpretation factor that is natural language information in the candidate interpretation factor. The operation receiving unit may present, as auxiliary information for setting the interpretation factor, a generic name that affects the evaluation of the user of the output of the predictor 110 and the evaluation target data 300, using existing techniques such as Internet Retrieval and Text Retrieval.

The setting button 2336 is an operation button for setting the interpretation factor set in the interpretation factor setting field 2335. When the setting button 2336 is operated, the terminal 101 transmits a setting request including identification information of the candidate interpretation factor and an interpretation factor, which are designated by the user. In this case, the conversion table generation unit 1402 sets the interpretation factor contained in the setting request to the field of the interpretation factor 1909 of the entry of the candidate interpretation factor information 1530.

The discarding button 2337 is an operation button for discarding the candidate interpretation factor. When the discarding button 2337 is operated, the terminal 101 transmits a discarding request including identification information of the candidate interpretation factor designated by the user. In this case, the conversion table generation unit 1402 deletes the entry of the candidate interpretation factor information 1530. The conversion table generation unit 1402 updates the value of the number of candidate interpretations 2312 and the value of the number of pieces of unclassified data 2313 along with the deletion of the entry.

The output button 2304 is an operation button for instructing generation of the conversion table 500. When the output button 2304 is operated, the terminal 101 transmits a conversion table output request to the operation receiving unit.

In the following description, a deletion request, a modification request, a setting request, and a discarding request are not distinguished and are also referred to as an information update request. The confirmation screen 2300 has been described above. The description will be returned to FIG. 15.

When the conversion table output request is received, the conversion table generation unit 1402 generates the conversion table 500 based on the area division information 1520 and the candidate interpretation factor information 1530 updated based on the input of the user, and stores the conversion table 500 in the interpretation factor conversion information 132.

Next, the processing executed in the computer system will be described in detail. First, processing executed by the candidate interpretation factor generation unit 1401 will be described.

Figure 24A:
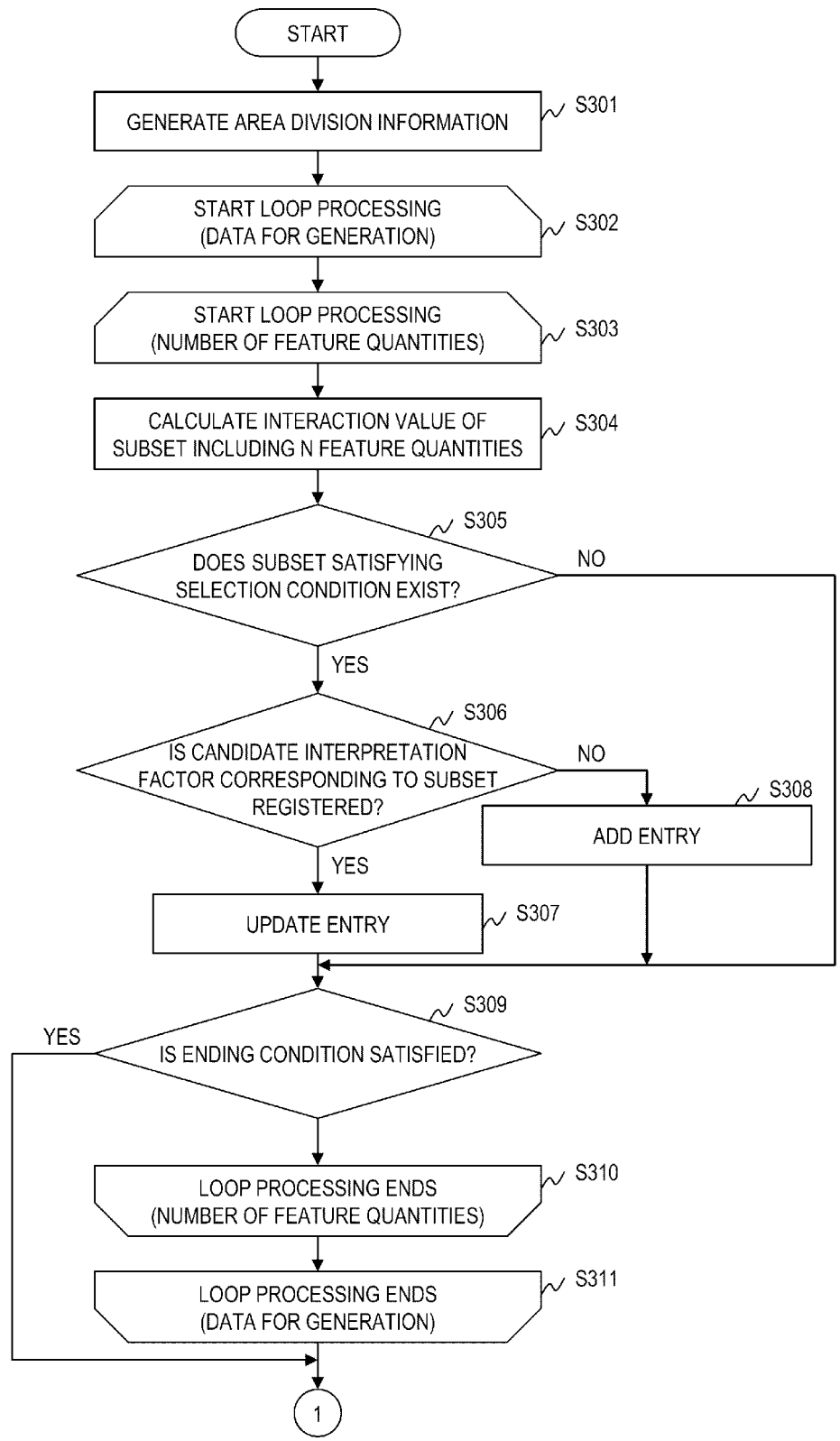
FIG. 24A is a flowchart showing an example of processing executed by a candidate interpretation factor generation unit according to the second embodiment.
Figures 24B, 25:
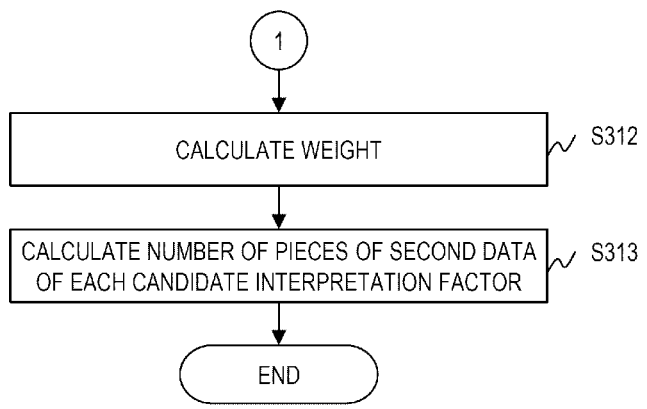
FIG. 24B is a flowchart showing the example of the processing executed by the candidate interpretation factor generation unit according to the second embodiment.
FIG. 25 shows an example of a data structure of an interaction value list according to the second embodiment.

FIGS. 24A and 24B are flowcharts showing an example of processing executed by the candidate interpretation factor generation unit 1401 according to the second embodiment. FIG. 25 is a diagram showing an example of a data structure of the interaction value list 2500 according to the second embodiment.

The candidate interpretation factor generation unit 1401 generates the area division information 1520 based on the area condition information, the data for generation 1500, and the contribution value data 600 (step S301). Specifically, the following processing is executed.

(Processing B1) The candidate interpretation factor generation unit 1401 selects a target feature quantity from the feature quantities contained in the data for generation 1500.

(Processing B2) The candidate interpretation factor generation unit 1401 specifies, based on the data for generation 1500 and the contribution value data 600, the value range of a value of the target feature quantity and the value range of the contribution value.

(Processing B3) The candidate interpretation factor generation unit 1401 divides the value range of the value of the target feature quantity into a plurality of areas and divides the value range of the contribution value of the target feature quantity into a plurality of areas, based on the division condition information. For example, the following processing is executed.

When the radio button 2141 is operated, the candidate interpretation factor generation unit 1401 equally divides the area of the value of the target feature quantity into the specified number. When the radio button 2142 is operated, the candidate interpretation factor generation unit 1401 calculates the statistic of the value of the target feature quantity, and equally divides the value area of the value into two parts based on the statistic. When the radio button 2143 is operated, the candidate interpretation factor generation unit 1401 divides the area of the value of the target feature quantity by the specified number so that the number of data for generation 1500 contained in each area is the same or different.

(Processing B4) The candidate interpretation factor generation unit 1401 adds an entry to the area division information 1520, and sets the identification information of the target feature quantity in the feature quantity 1801 of the added entry. The candidate interpretation factor generation unit 1401 sets division results for the division area (value) 1802 and the division area (contribution value) 1803 of the added entry.

(Processing B5) When the processing is not completed for all the feature quantities, the candidate interpretation factor generation unit 1401 returns to (processing B1). When the processing is completed for all the feature quantities, the candidate interpretation factor generation unit 1401 terminates the processing in step S301.

The candidate interpretation factor generation unit 1401 may divide an area based on a value such as the output value 1705 of the intermediate calculation data 1510 as necessary. The processing in step S301 has been described above.

Next, the candidate interpretation factor generation unit 1401 starts the loop processing of the data for generation 1500 (step S302).

Specifically, the candidate interpretation factor generation unit 1401 selects one data for generation 1500, from the unprocessed data for generation 1500, as the target data for generation 1500.

Next, the candidate interpretation factor generation unit 1401 starts the loop processing of the number of feature quantities (step S303).

Specifically, the candidate interpretation factor generation unit 1401 sets the value set in the check field 2125 to a variable n as an initial value. The candidate interpretation factor generation unit 1401 initializes the interaction value list 2500. When the check field 2125 is not operated, a preset value, for example, "2" is set therein.

The interaction value list 2500 includes entries formed of an ID 2501, an intermediate compute data ID 2502, a subset 2503, and an interaction value 2504. One entry corresponds to the interaction value data.

A field of the ID 2501 stores identification information of the interaction value data. A field of the intermediate calculation data ID 2502 stores identification information of the intermediate calculation data 1510 used in calculating the interaction value. The field of the intermediate calculation data ID 2502 stores the same identification information as that of the field of the ID 1701. The field of the subset 2503 stores a subset of feature quantities as calculation target for interaction values. A field of the interaction value 2504 stores the interaction values.

In step S303, all entries in the interaction value list 2500 are deleted. The processing in step S303 has been described above.

Next, the candidate interpretation factor generation unit 1401 calculates an interaction value of a subset including n feature quantities (step S304). Specifically, the following processing is executed.

(Processing C1) The candidate interpretation factor generation unit 1401 generates a subset including n feature quantities.

(Processing C2) The candidate interpretation factor generation unit 1401 selects a target subset from the generated subsets.

(Processing C3) The candidate interpretation factor generation unit 1401 calculates an interaction value of the target subset. The method of calculating the interaction value is described in Non-Patent Literature 2 and Non-Patent Literature 3, so that a detailed description thereof is omitted. Alternatively, the interaction value is calculated as follows.

The candidate interpretation factor generation unit 1401 retrieves the intermediate calculation data 1510 in which the subset 1703 corresponds to the union of a subset M of complement of the target subset and a subset L of the target subset. The candidate interpretation factor generation unit 1401 calculates a weighted average of the output values 1705 of the retrieved intermediate calculation data 1510 as an interaction value.

The weight can be calculated as follows. (1) The factorial of a value obtained by subtracting the total of the number of elements in the subset M and the number of elements in the target subset from the total number N of the feature quantities contained in the data for generation is multiplied by the factorial of the number of elements in the subset. (2) The value of (1) is divided by a value obtained by adding 1 to the value obtained by subtracting the number of elements in the target subset from N. (3) When the number of elements in a complement set of the subset L is an odd number, the value of (2) is multiplied by −1.

(Processing C4) The candidate interpretation factor generation unit 1401 adds an entry to the interaction value list 2500, and sets the identification information of the interaction value data in the field of the ID 2501 of the added entry. The candidate interpretation factor generation unit 1401 sets identification information of the intermediate calculation data 1510 in the field of the intermediate calculation data ID 2502 of the added entry. The candidate interpretation factor generation unit 1401 sets a target subset in the field of the subset 2503 of the added entry, and sets the calculated interaction value to the field of the interaction value 2504.

(Processing C5) When the processing is not completed for all subsets, the candidate interpretation factor generation unit 1401 returns to (processing C2). When the processing is completed for all subsets, the candidate interpretation factor generation unit 1401 terminates the processing in step S304. The processing in step S304 has been described above.

Next, the candidate interpretation factor generation unit 1401 determines whether a subset satisfying the adoption condition exists (step S305). In the present embodiment, the determination in step S305 is performed based on an interaction value. For example, the following determination is performed in the present embodiment.

When the radio button 2131 is operated, the candidate interpretation factor generation unit 1401 determines that the adoption condition is satisfied. In this case, a predetermined number of subsets having large values in the field of the interaction value 2504 are selected.

When the radio button 2132 is operated, the candidate interpretation factor generation unit 1401 calculates a ratio of the interaction value 2504 to the predicted value of the target data for generation 1500. When an entry whose ratio is larger than the threshold exists, the candidate interpretation factor generation unit 1401 determines that a subset satisfying the adoption condition exists.

When the radio button 2133 is operated, the following determination is performed. When the interaction value 2504 corresponding to a subset is significantly larger than the interaction value 2504 corresponding to another subset having the same number of elements as the subset with the specific value of the interaction value 2504 being set as the significance level, the candidate interpretation factor generation unit 1401 determines that a subset satisfying the adoption condition exists.

When it is determined that the subset satisfying the adoption condition does not exist, the candidate interpretation factor generation unit 1401 proceeds to step S309.

When it is determined that a subset satisfying the adoption condition exists, the candidate interpretation factor generation unit 1401 determines whether the candidate interpretation factor corresponding to the subset is registered in the candidate interpretation factor information 1530 (step S306).

Specifically, the candidate interpretation factor generation unit 1401 determines, by referring to the field of the area (value) 1903 and the field of the area (contribution value) 1904, whether there exists an entry matching a combination of areas to which the values of the feature quantities constituting the subset satisfying the adoption condition belongs and a combination of areas to which the contribution values of the feature quantities constituting the subset satisfying the adoption condition belongs. When an entry satisfying the above condition exists, the candidate interpretation factor generation unit 1401 determines that the candidate interpretation factor corresponding to the subset satisfying the adoption condition is registered in the candidate interpretation factor information 1530.

When it is determined that the candidate interpretation factor corresponding to the subset satisfying the adoption condition is registered in the candidate interpretation factor information 1530, the candidate interpretation factor generation unit 1401 updates the entry corresponding to the candidate interpretation factor (step S307), and then the processing proceeds to step S309.

Specifically, the candidate interpretation factor generation unit 1401 adds a combination of the identification information and the interaction value of the target data for generation 1500 selected in step S302 to the field of the interaction value 1908 of the entry corresponding to the candidate interpretation factor. The candidate interpretation factor generation unit 1401 adds 1 to the number of pieces of the first data 1906 of the entry.

When it is determined that the candidate interpretation factor corresponding to the subset satisfying the adoption condition is not registered in the candidate interpretation factor information 1530, the candidate interpretation factor generation unit 1401 adds an entry corresponding to the candidate interpretation factor to the candidate interpretation factor information 1530 (step S307), and then the processing proceeds to step S309. Specifically, the following processing is executed.

(Processing D1) The candidate interpretation factor generation unit 1401 adds an entry to the candidate interpretation factor information 1530. The candidate interpretation factor generation unit 1401 sets the identification information in the field of the ID 1901 of the added entry, sets "1" in the field of the number of pieces of the first data 1906, and sets "0" in the field of the number of pieces of the first data 1906. The candidate interpretation factor generation unit 1401 sets a combination of the identification information and the interaction value of the target data for generation 1500 selected in step S302 in the field of the interaction value 1908 of the added entry.

(Processing D2) The candidate interpretation factor generation unit 1401 generates the same number of rows as the number of elements of the target subset in the field of the feature quantity 1902, the field of the area (value) 1903, the field of the area (contribution value) 1904, and the field of the weight 1905 of the added entry. The candidate interpretation factor generation unit 1401 sets the identification information of the feature quantity, which is an element of the target subset, in the field of the feature quantity 1902 of the added entry.

(Processing D3) The candidate interpretation factor generation unit 1401 selects a target feature quantity from the feature quantities constituting the target subset. The candidate interpretation factor generation unit 1401 retrieves an entry whose feature quantity 1801 corresponds to the target feature quantity, by referring to the area division information 1520.

(Processing D4) The candidate interpretation factor generation unit 1401 specifies an area including the value of the target feature quantity of the target data for generation 1500 selected in step S302 by referring to the division area (value) 1802 of the retrieved entry. The candidate interpretation factor generation unit 1401 sets the specified area in the field of the area (value) 1903 of a row corresponding to the target feature quantity of the added entry.

(Processing D5) The candidate interpretation factor generation unit 1401 specifies an area including a contribution value of the target feature quantity of the target data for generation 1500 selected in step S302 by referring to the division area (contribution value) 1803 of the retrieved entry. The candidate interpretation factor generation unit 1401 sets the specified area in the field of the area (contribution value) 1904 of a row corresponding to the target feature quantity of the added entry.

(Processing D6) When the processing is not completed for all the feature quantities constituting the target subset, the candidate interpretation factor generation unit 1401 returns to (processing D3). When the processing is completed for all the feature quantities constituting the target subset, the candidate interpretation factor generation unit 1401 terminates the processing in step S307. The processing in step S307 has been described above.

In step S309, the candidate interpretation factor generation unit 1401 determines whether the termination condition is satisfied (step S309). For example, the following determination is performed in the present embodiment.

When the check field 2122 is operated, the candidate interpretation factor generation unit 1401 determines whether the number of entries of the candidate interpretation factor information 1530 (the number of candidate interpretation factors) matches the upper limit value. When the number of entries of the candidate interpretation factor information 1530 matches the upper limit value, the candidate interpretation factor generation unit 1401 determines that the termination condition is satisfied.

When the check field 2123 is operated, the candidate interpretation factor generation unit 1401 determines whether the calculation time is equal to or longer than the threshold. When the calculation time is equal to or longer than the threshold, the candidate interpretation factor generation unit 1401 determines that the termination condition is satisfied.

When it is determined that the end condition is satisfied, the candidate interpretation factor generation unit 1401 stops the loop processing and the processing proceeds to step S312. At this time, when the candidate interpretation factor generated from the target data for generation 1500 does not exist, the candidate interpretation factor generation unit 1401 stores a combination of the identification information of the target data for generation 1500 and the unclassified flag in the work area.

When it is determined that the termination condition is not satisfied, the candidate interpretation factor generation unit 1401 determines whether the number of feature quantities matches the upper limit value (step S310). When the check field 2124 is operated, the upper limit value is a value set in the check field 2124. When the check field 2124 is not operated, the upper limit value is the total number of feature quantities of the data for generation 1500.

When it is determined that the number of feature quantities does not match the upper limit value, the candidate interpretation factor generation unit 1401 returns to step S303 and adds 1 to the value of the variable n.

When it is determined that the number of feature quantities matches the upper limit value, the candidate interpretation factor generation unit 1401 determines whether the processing is completed for all the data for generation 1500 (step S311). At this time, when the candidate interpretation factor generated from the target data for generation 1500 does not exist, the candidate interpretation factor generation unit 1401 stores a combination of the identification information of the target data for generation 1500 and the unclassified flag in the work area.

When it is determined that the processing is not completed for all the data for generation 1500, the candidate interpretation factor generation unit 1401 returns to step S302 and selects new data for generation 1500.

When it is determined that the processing is completed for all the data for generation 1500, the candidate interpretation factor generation unit 1401 sets the weight of each candidate interpretation factor (step S312). For example, the following setting method can be considered.

(Setting Method 1) The candidate interpretation factor generation unit 1401 sets all weights of the candidate interpretation factors to "1". In this case, "1" is set in a row of the weight 1905 of each entry.

(Setting Method 2) The candidate interpretation factor generation unit 1401 sets a weight of a candidate interpretation factor based on an input of the user. In this case, the value input by the user is set in the row of the weight 1905 of each entry.

(Setting Method 3) The candidate interpretation factor generation unit 1401 calculates the weight of the candidate interpretation factor based on the combination of interaction values stored in the field of the interaction value 1908 of the entry corresponding to the candidate interpretation factor, and sets the weight. In this case, a value calculated based on the field of the interaction value 1908 of each entry is set in the row of the weight 1905 of each entry.

The present invention is not limited to the method of setting the weight.

Next, the candidate interpretation factor generation unit 1401 calculates the number of pieces of the second data of each candidate interpretation factor (step S313). Thereafter, the candidate interpretation factor generation unit 1401 terminates a series of processing. Specifically, the following processing is executed.

(Processing E1) The candidate interpretation factor generation unit 1401 determines whether there exists data for generation 1500 that is not processed in the loop processing of the data for generation 1500.

(Processing E2) When the data for generation 1500 that is not processed in the loop processing of the data for generation 1500 exists, the candidate interpretation factor generation unit 1401 specifies the corresponding candidate interpretation factor based on the value and the contribution value of each feature quantity of the unprocessed data for generation 1500. The candidate interpretation factor generation unit 1401 stores, in the work area, a combination of the identification information of the data for generation 1500 and the identification information (ID 1901) of the specified candidate interpretation factor. The candidate interpretation factor generation unit 1401 updates the field of the number of pieces of the first data 1906 of each entry of the candidate interpretation factor information 1530.

When the corresponding candidate interpretation factor does not exist, the candidate interpretation factor generation unit 1401 stores the combination of the identification information of the data for generation 1500 and the unclassified flag in the work area.

(Processing E3) When data for generation 1500 that is not processed in the loop processing of the data for generation 1500 does not exist or when the processing of (processing E2) is executed, the candidate interpretation factor generation unit 1401 specifies an interpretation factor of each data for generation 1500 by referring to the candidate interpretation factor information 1530. The candidate interpretation factor generation unit 1401 stores, in the work area, a combination of the identification information of the data for generation 1500 and the identification information (ID 1901) of the specified candidate interpretation factor.

(Processing E4) The candidate interpretation factor generation unit 1401 stores, in the work area, the number of pieces of combinations including the unclassified flag as the number of pieces of unclassified data.

(Processing E5) The candidate interpretation factor generation unit 1401 specifies a set including only one candidate interpretation factor. The candidate interpretation factor generation unit 1401 generates a group of the specified combination for each type of candidate interpretation factor. The candidate interpretation factor generation unit 1401 sets the number of combinations contained in the group in the field of the second data 1907 of the entry corresponding to each group by referring to the candidate interpretation factor information 1530.

When the check field 2126 is operated, the candidate interpretation factor generation unit 1401 deletes the entry whose value in the field of the number of pieces of the first data 1906 is smaller than the threshold before the processing E3 is executed, and executes the processing of (processing E2) again.

The candidate interpretation factor generation unit 1401 may calculate the number of pieces of the second data 1907 based on a value such as the output value 1705 of the intermediate calculation data 1510 as necessary. The processing in step S313 has been described above.

Figures 26, 27:
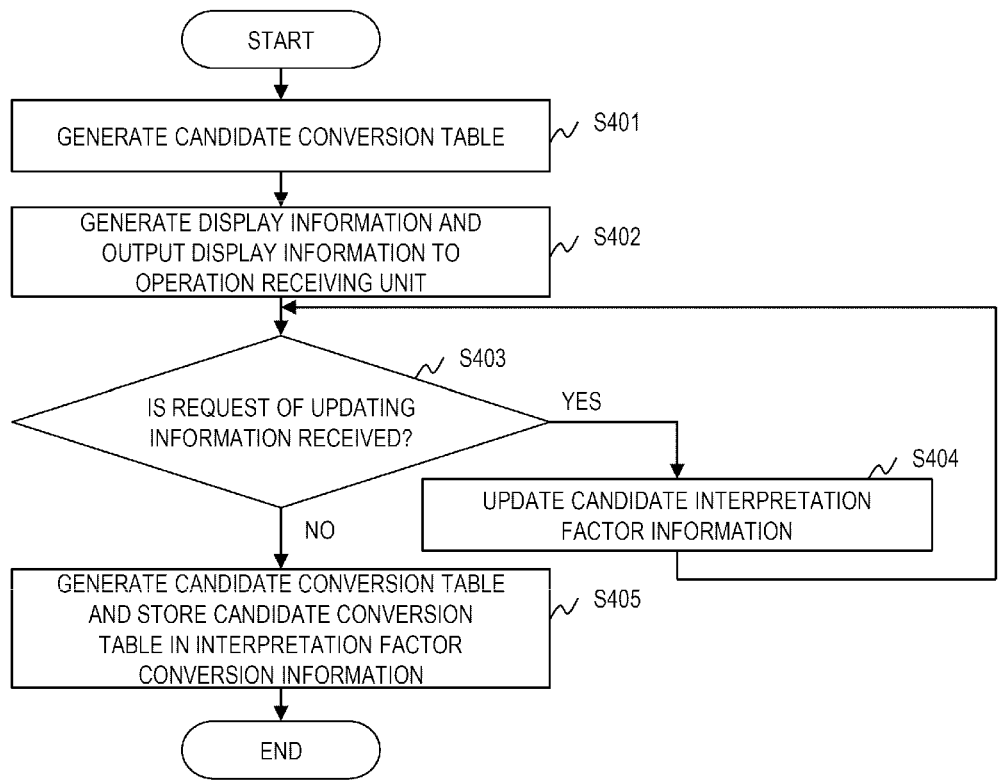
FIG. 26 shows processing executed by a conversion table generation unit according to the second embodiment.
FIG. 27 shows an example of a data structure of candidate interpretation factor information according to a third embodiment.

FIG. 26 is a flowchart showing processing executed by the conversion table generation unit 1402 according to the second embodiment.

The conversion table generation unit 1402 generates a candidate conversion table 1540 based on the area division information 1520 and the candidate interpretation factor information 1530 (step S401). Specifically, the following processing is executed.

(Processing F1) The conversion table generation unit 1402 generates, based on the area division information 1520, a matrix format candidate conversion table 1540 in which the area of the value of the feature quantity is set as a column component and the area of the contribution value of the feature quantity is set as a row component. At this time point, the candidate interpretation factor data 2000 does not exist in any of the candidate conversion tables 1540.

(Processing F2) The conversion table generation unit 1402 selects a target entry from the candidate interpretation factor information 1530.

(Processing F3) The conversion table generation unit 1402 selects a target feature quantity from the feature quantities contained in the target entry.

(Processing F4) The conversion table generation unit 1402 specifies a cell of the candidate conversion table 1540 corresponding to the target feature quantity based on the area (value) 1903 and the area (contribution value) 1904 of the row corresponding to the target feature quantity. The conversion table generation unit 1402 sets the candidate interpretation factor data 2000 that includes identification information of the candidate interpretation factor and the value in the field of the weight 1905 of the row corresponding to the target feature quantity in the specified cell.

(Processing F5) When the processing is not completed for all the feature quantities contained in the target entry, the conversion table generation unit 1402 returns to (processing F3). When the processing is completed for all the feature quantities contained in the target entry, the conversion table generation unit 1402 determines whether the processing is completed for all the entries of the candidate interpretation factor information 1530.

(Processing F6) When the processing is not completed for all the entries of the candidate interpretation factor information 1530, the conversion table generation unit 1402 returns to (processing F2). When the processing is completed for all the entries of the candidate interpretation factor information 1530, the conversion table generation unit 1402 terminates the processing of step S401. The processing in step S401 has been described above.

Next, the conversion table generation unit 1402 generates display information for displaying the candidate conversion table 1540, the candidate interpretation factor information 1530, and the like, and outputs the display information to the operation receiving unit (step S402). Accordingly, the confirmation screen 2300 is displayed on the terminal 101. Thereafter, the conversion table generation unit 1402 shifts to a waiting state.

When receiving a request via the confirmation screen 2300, the conversion table generation unit 1402 determines whether the received request is a request of updating information (step S403).

When it is determined that the received request is a request of updating information, the conversion table generation unit 1402 updates the candidate interpretation factor information 1530 according to the content of the request of updating information (step S404). Thereafter, the conversion table generation unit 1402 returns to step S403. In step S404, for example, the following processing is executed.

When the request of updating information is a deletion request, the conversion table generation unit 1402 searches for an entry corresponding to the identification information of the candidate interpretation factor contained in the deletion request from the candidate interpretation factor information 1530, and deletes the row corresponding to the identification information of the feature quantity contained in the deletion request from the retrieved entry.

When the request of updating information is a modification request, the conversion table generation unit 1402 retrieves an entry corresponding to the identification information of the candidate interpretation factor contained in the modification request from the candidate interpretation factor information 1530, and updates the field of the weight 1905 of the row corresponding to the identification information of the feature quantity contained in the modification request of the searched entry.

When the request of updating information is a setting request, the conversion table generation unit 1402 retrieves an entry corresponding to the identification information of the candidate interpretation factor contained in the setting request from the candidate interpretation factor information 1530, and sets the interpretation factor in the field of the interpretation factor 1909 of the row corresponding to the identification information of the feature quantity contained in the setting request of the searched entry.

When the request of updating information is a discarding request, the conversion table generation unit 1402 retrieves an entry corresponding to the identification information of the candidate interpretation factor contained in the discarding request from the candidate interpretation factor information 1530, and deletes the entry.

The conversion table generation unit 1402 may update the candidate conversion table 1540 based on the request of updating information.

When the request of updating information is a deletion request, the conversion table generation unit 1402 deletes the candidate interpretation factor data 2000 corresponding to the identification information of the candidate interpretation factor contained in the deletion request, from the candidate conversion table 1540 corresponding to the identification information of the feature quantity contained in the deletion request.

When the request of updating information is a modification request, the conversion table generation unit 1402 retrieves candidate interpretation factor data 2000 corresponding to the identification information of the candidate interpretation factor contained in the modification request, from the candidate conversion table 1540 corresponding to the identification information of the feature quantity contained in the modification request. The conversion table generation unit 1402 updates the value of the weight 2002 of the retrieved candidate interpretation factor data 2000.

When the request of updating information is a setting request, the conversion table generation unit 1402 retrieves the candidate interpretation factor data 2000 corresponding to the identification information of the candidate interpretation factor contained in the modification request from the candidate conversion table 1540 corresponding to the identification information of the feature quantity contained in the modification request. The conversion table generation unit 1402 replaces the interpretation factor ID 2001 of the retrieved candidate interpretation factor data 2000 with an interpretation factor.

When the request of updating information is a discarding request, the conversion table generation unit 1402 deletes the candidate interpretation factor data 2000 corresponding to the identification information of the candidate interpretation factor contained in the discarding request, from each candidate conversion table 1540. The processing in step S404 has been described above.

When it is determined that the received request is not a request of updating information, that is, when it is determined that the received request is a conversion table output request, the conversion table generation unit 1402 generates the conversion table 500 based on the area division information 1520 and the candidate interpretation factor information 1530, and stores the conversion table 500 generated in the interpretation factor conversion information 132 (step S405). Thereafter, the conversion table generation unit 1402 terminates the processing.

The method of generating the conversion table 500 is similar to that of the candidate conversion table 1540. However, in (processing F4), the conversion table generation unit 1402 sets, in the specified cell, the interpretation factor data 510 including the value in the field of the interpretation factor 1909 of the target entry and the value in the field of the weight 1905 of the row corresponding to the target feature quantity.

When the candidate conversion table 1540 is updated based on the request of updating information in step S404, the candidate conversion table 1540 may be output as the conversion table 500 in the interpretation factor conversion information 132.

The conversion table generation unit 1402 generates the conversion table 500, and then transmits a storage request including the conversion table 500 to the computer 100-3. The interpretation factor selection unit 130 or the result output unit 131 of the computer 100-3 stores the conversion table 500 in the interpretation factor conversion information 132.

According to the second embodiment, the computer system can generate the conversion table 500 for each feature quantity from the data for generation 1500 without omission, based on an objective criterion. The interpretation information 610 generated based on the conversion table 500 generated in this way is useful as information indicating the basis of the predicted value of the evaluation target data 300 that is objective and has no omission.

Third Embodiment

In the third embodiment, a method of generating a candidate interpretation factor is partially different. Specifically, similar candidate interpretation factors are integrated. Hereinafter, a third embodiment will be described focusing on a difference from the second embodiment.

The configuration of the computer system according to the third embodiment, the hardware configuration and the software configuration of the computer 100, and the flow of processing of the computer system are the same as those in the second embodiment, so that the descriptions thereof are omitted.

In the third embodiment, a data structure of the candidate interpretation factor information 1530 is different. FIG. 27 shows an example of a data structure of the candidate interpretation factor information 1530 according to the third embodiment.

For ease of description, the field of the area (value) 1903, the field of the area (contribution value) 1904, the field of the weight 1905, the field of the number of pieces of the first data 1906, the field of the number of pieces of the second data 1907, the field of the interaction value 1908, and the field of the interpretation factor 1909 are omitted.

An entry stored in the candidate interpretation factor information 1530 according to the third embodiment includes a field of integration ID 1910 and a field of integration type 1911. The field of integration ID 1910 stores identification information set in integrated candidate interpretation factors. The field of integration type 1911 stores the type of integrated conditions. In the field of integration type 1911 of the entry in which the identification information is set in the field of integration ID 1910, either of the terms "normal" and "special" is stored.

Figure 28A:
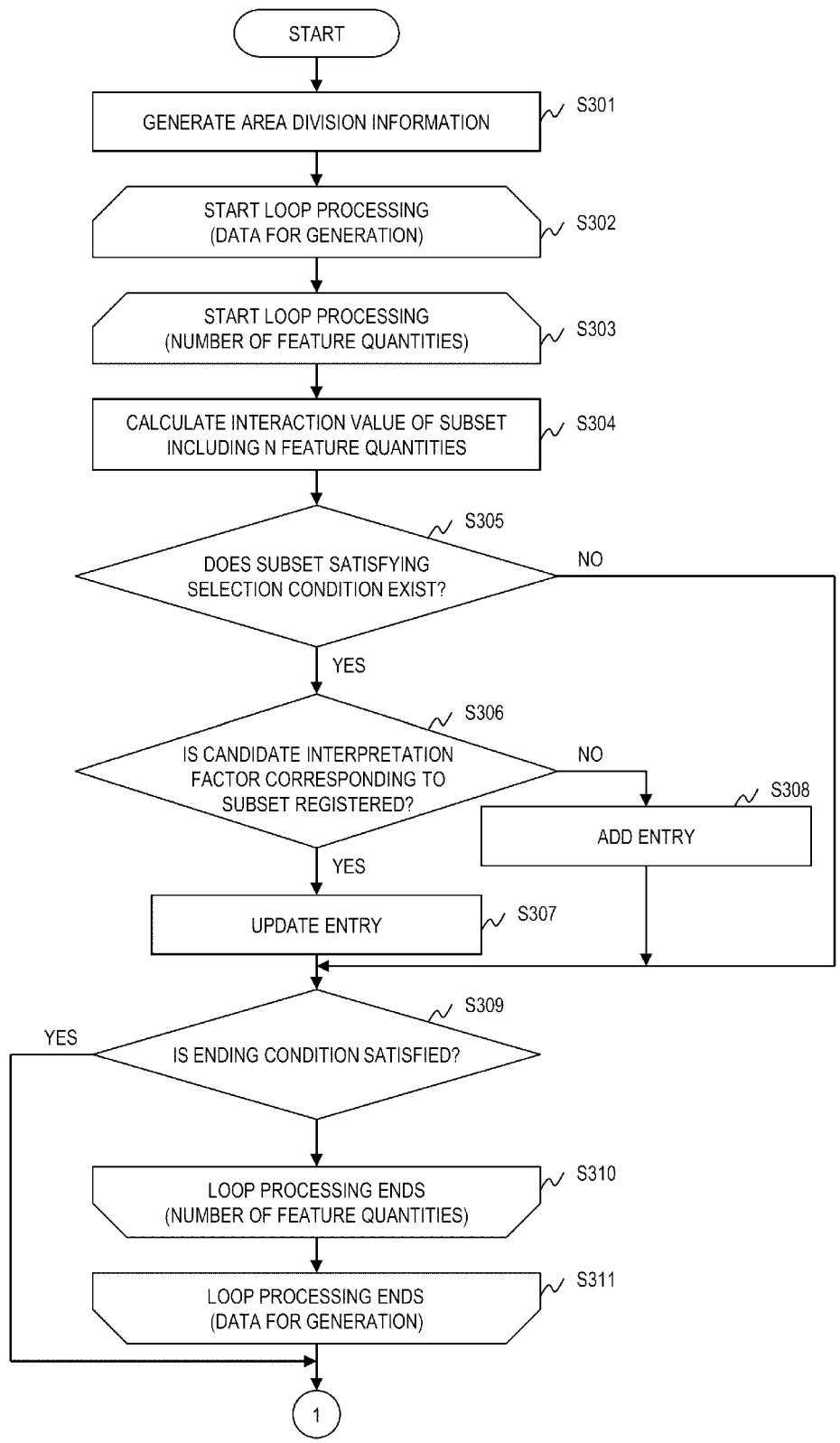
FIG. 28A is a flowchart showing an example of processing executed by a candidate interpretation factor generation unit according to the third embodiment.
Figure 28B:
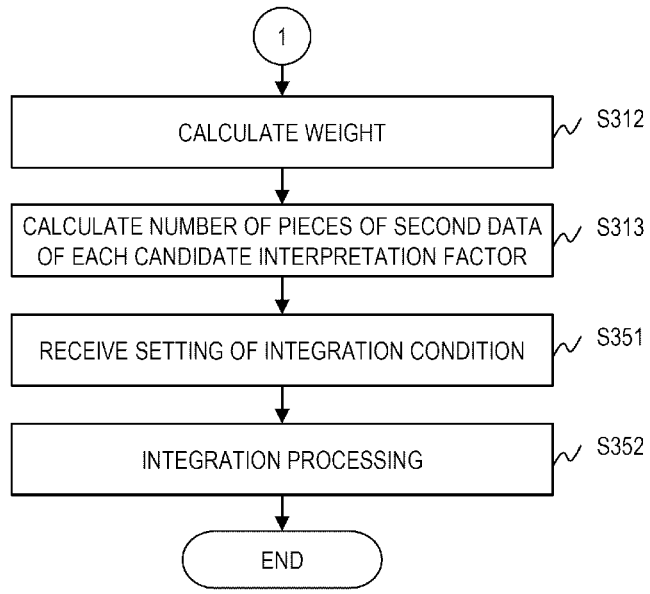
FIG. 28B is a flowchart showing the example of the processing executed by the candidate interpretation factor generation unit according to the third embodiment.
Figure 29:
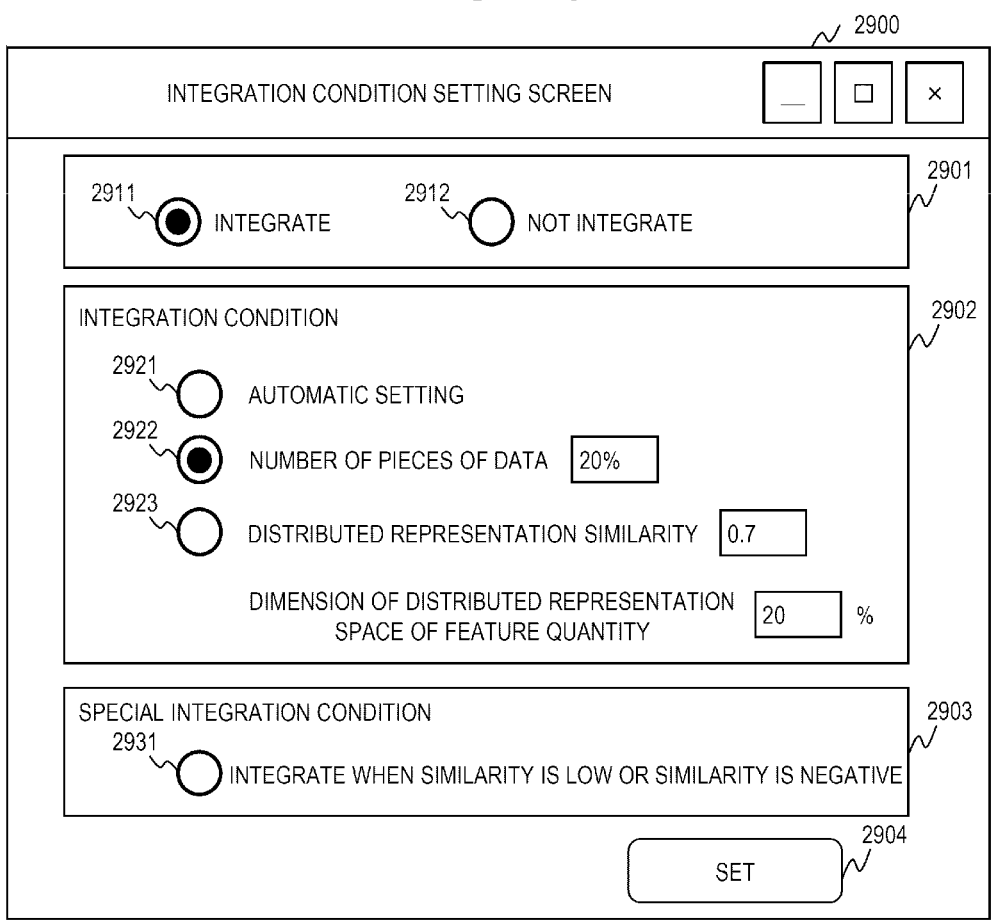
FIG. 29 shows an example of an integration condition setting screen displayed on a terminal according to the third embodiment.

FIGS. 28A and 28B are flowcharts showing an example of processing executed by the candidate interpretation factor generation unit 1401 according to the third embodiment. FIG. 29 shows an example of an integration condition setting screen 2900 displayed on the terminal 101 according to the third embodiment. FIG. 30 shows an example of an integration confirmation screen 3000 displayed on the terminal 101 according to the third embodiment.

The processing from step S301 to step S313 is the same as the processing described in the second embodiment. In the third embodiment, the candidate interpretation factor generation unit 1401 receives setting of an integration condition after the processing of step S313 is executed (step S351).

Specifically, the candidate interpretation factor generation unit 1401 generates display information for displaying the integration condition setting screen 2900, and outputs the display information to the operation receiving unit. The operation receiving unit transmits the display information to the terminal 101. Here, the integration condition setting screen 2900 will be described.

The integration condition setting screen 2900 is a screen presented by the operation receiving unit, and is displayed on the terminal 101. The integration condition setting screen 2900 includes an integration availability selection field

2901, an integration condition setting field 2902, a special integration condition setting field 2903, and a setting button 2904.

The integration availability selection field 2901 is a field for selecting whether to integrate candidate interpretation factors. The value in the integration availability selection field 2901 is output as integration availability information. The integration availability selection field 2901 includes radio buttons 2911 and 2912.

The radio button 2911 is a radio button operated to integrate candidate interpretation factors. The user operates the radio button 2911 to perform an input to the integration condition setting field 2902 and the special integration condition setting field 2903. The radio button 2912 is a radio button operated not to integrate the candidate interpretation factors. When the radio button 2912 is operated, the input to the integration condition setting field 2902 and the special integration condition setting field 2903 is invalidated.

The integration condition setting field 2902 is a field for setting an integration condition of the candidate interpretation factor. The value in the integration condition setting field 2902 is output as integration condition setting information. The integration condition setting field 2902 includes radio buttons 2921, 2922, and 2923.

The radio button 2921 is a radio button operated to set a predefined integration condition.

The radio button 2922 is a radio button operated to integrate the candidate interpretation factors based on the number of pieces of first data and the number of pieces of second data. The user operates the radio button 2922 to set the number of pieces of first data or a ratio of the number of pieces of first data to the number of pieces of second data.

The radio button 2923 is a radio button operated to integrate the candidate interpretation factors based on the similarity between the candidate interpretation factors in distributed representation space. The user operates the radio button 2923 to set a threshold of the similarity and a dimension of the distributed representation space. In the present embodiment, the candidate interpretation factor generation unit 1401 generates a distributed representation of the data for generation 1500 by latent representation of the data for generation 1500 based on the dimension of the distributed space, and calculates the similarity between the sets of feature quantities constituting each candidate interpretation factor (similarity between candidate interpretation factors) by using the distributed representation. Instead of the dimension of the distributed representation space, parameters used for other latent representations may be input.

The special integration condition setting field 2903 is a field for setting an integration condition different from that of the integration condition setting field 2902. The value in the special integration condition setting field 2903 is output as special integration condition setting information. The special integration condition setting field 2903 includes a radio button 2931.

The radio button 2931 is a radio button operated to integrate candidate interpretation factors whose similarity is low or is a negative value in the integration condition corresponding to the radio button 2923. The candidate interpretation factor that satisfies the special integration condition information is integrated as a candidate interpretation factor having an opposite meaning.

The setting button 2904 is an operation button for setting values set in the integration availability selection field 2901, the integration condition setting field 2902, and the special integration condition setting field 2903. When the setting button 2904 is operated, the terminal 101 transmits a setting request including the integration availability information, the integration condition setting information, and the special integration condition setting information.

The integration condition setting screen 2900 may include an operation button for saving, in the computer 100-2, the integrated condition setting information, the integration condition setting information, and the special integration condition setting information, which are set via the integration condition setting screen 2900, and an operation button for instructing the destruction or initialization of the information.

The integration condition setting screen 2900 has been described above. The description returns to FIG. 28B.

When receiving the setting request from the operation receiving unit, the candidate interpretation factor generation unit 1401 executes integration processing based on the integration availability information, the integration condition setting information, and the special integration condition setting information contained in the setting request (step S352). Thereafter, the candidate interpretation factor generation unit 1401 terminates the processing. Specifically, the following processing is executed.

(Processing G1) The candidate interpretation factor generation unit 1401 determines whether the integration availability information includes a value corresponding to the radio button 2912. When the integration availability information includes a value corresponding to the radio button 2912, the candidate interpretation factor generation unit 1401 terminates the integration processing without integrating the candidate interpretation factors.

(Processing G2) When the integration availability information includes a value corresponding to the radio button 2911, the candidate interpretation factor generation unit 1401 calculates an index used to integrate candidate interpretation factors based on the integration condition setting information.

When the integration condition setting information includes a value corresponding to the radio button 2922, the candidate interpretation factor generation unit 1401 calculates the number of pieces of first data of each candidate interpretation factor or a ratio of the number of pieces of first data to the number of pieces of second data. When the integration condition setting information includes a value corresponding to the radio button 2923, the candidate interpretation factor generation unit 1401 calculates the similarity between the candidate interpretation factors.

(Processing G3) The candidate interpretation factor generation unit 1401 specifies, based on a comparison result between the calculated index and the threshold, a set of candidate interpretation factors that can be integrated. In addition, the candidate interpretation factor generation unit 1401 specifies, based on the calculated index and the special integration condition setting information, a set of candidate interpretation factors that can be integrated. The candidate interpretation factor generation unit 1401 stores, in a work area, information of a set of specified interpretation factors.

(Processing G4) The candidate interpretation factor generation unit 1401 generates display information for presenting the set of specified candidate interpretation factors, and outputs the generated display information to the operation receiving unit. Accordingly, the integration confirmation screen 3000 is displayed on the terminal 101. The candidate interpretation factor generation unit 1401 integrates a set of candidate interpretation factors based on an operation via the integration confirmation screen 3000. Here, the integration confirmation screen 3000 will be described.

The integration confirmation screen 3000 is a screen presented by the operation receiving unit, and is displayed on the terminal 101. The integration confirmation screen 3000 includes an integration target display field 3001, a candidate interpretation factor detail display field 3002, an integration button 3003, a discarding button 3004, a next button 3005, and a completion button 3006.

The integration target display field 3001 is a field for displaying information on the specified candidate interpretation factor and a determination basis. The integration target display field 3001 includes a candidate interpretation factor display field 3011 and an index display field 3012.

The candidate interpretation factor display field 3011 is a field for displaying identification information of the specified candidate interpretation factor. The index display field 3012 is a field for displaying an index used during determination.

The candidate interpretation factor detail display field 3002 displays detailed data of the specified candidate interpretation factor.

The integration button 3003 is a button operated to integrate a set of candidate interpretation factors displayed on the integration confirmation screen 3000. When the integration button 3003 is operated, the terminal 101 transmits an integration request including information of the set of candidate interpretation factors.

When receiving the integration request, the candidate interpretation factor generation unit 1401 specifies an entry group to be integrated from the candidate interpretation factor information 1530 based on the information of the set of candidate interpretation factors contained in the integration request. The candidate interpretation factor generation unit 1401 sets the same identification information as that of the field of integration ID 1910 of the specified entry group, and sets either of the terms "normal" and "special" in the field of integration type 1911. The term "normal" is set in the field of integration type 1911 when the candidate interpretation factors are integrated based on the integration condition setting information. The term "special" is set in the field of integration type 1911 when the candidate interpretation factors are integrated based on the special integration condition setting information.

The discarding button 3004 is a button operated not to integrate the set of candidate interpretation factors displayed on the integration confirmation screen 3000. When the discarding button 3004 is operated, the terminal 101 transmits a discarding request including information of the set of candidate interpretation factors.

When receiving the discarding request, the candidate interpretation factor generation unit 1401 deletes the information of the set of candidate interpretation factors contained in the discarding request from the work area.

The next button 3005 is a button operated to display information of a next set of interpretation factors.

The completion button 3006 is a button operated to terminate the operation via the integration confirmation screen 3000. When the completion button 3006 is operated, the terminal 101 transmits a completion notification.

The integration confirmation screen 3000 has been described above. The integration processing will be described again.

(Processing G5) When receiving the completion notification, the candidate interpretation factor generation unit 1401 terminates the integration processing. The processing in step S352 has been described above.

The candidate interpretation factor generation unit 1401 may automatically integrate the set of specified candidate interpretation factors without displaying the integration confirmation screen 3000.

In the processing of generating the conversion table 500 (FIG. 26), the conversion table generation unit 1402 sets the value set in the field of integration ID 1910 in the interpretation factor ID 2001 of the candidate interpretation factor data 2000 corresponding to the integrated candidate interpretation factor. The conversion table generation unit 1402 sets the same interpretation factor for the candidate interpretation factor whose identification information is set in the field of integration ID 1910.

According to the third embodiment, the computer system can avoid generation of duplicate or similar interpretation factors by integrating a plurality of candidate interpretation factors. In addition, the calculation efficiency can be improved.

The invention is not limited to the above-described embodiment, and includes various modifications. In addition, for example, the above-described embodiment has been described in detail for easy understanding of the invention, and the invention is not necessarily limited to those including all the configurations described above. In addition, a part of the configuration of each embodiment can be added, deleted, or replaced with another configuration.

Each of the configurations, functions, processing units, processing methods described above may be partially or entirely implemented by hardware such as by designing with an integrated circuit. Further, the invention can also be implemented by program code of software that implements the functions of the embodiments. In this case, a storage medium storing the program code is provided to a computer, and a processor provided in the computer reads out the program code stored in the storage medium. In this case, the program code itself read out from the storage medium implements the functions of the embodiments described above, and the program code itself and the storage medium storing the program code constitute the invention. Examples of the storage medium for supplying such a program code include a flexible disk, a CD-ROM, a DVD-ROM, a hard disk, a solid state drive (SSD), an optical disk, a magneto-optical disk, a CD-R, a magnetic tape, a nonvolatile memory card, and a ROM.

For example, the program code that implements the function described in the present embodiment can be implemented by a wide range of programs or scripting languages, such as an assembler, C/C++, perl, Shell, PHP, and Java (registered trademark).

Further, the program code of the software implementing the functions of the embodiments is distributed via a network, so that the program code is stored in a storage unit such as the hard disk or the memory of the computer or in a storage medium such as a CD-RW or the CD-R. The processor provided in the computer may read out and execute the program code stored in the storage unit or the storage medium.

In the embodiment described above, the control lines and the information lines are considered to be necessary for description, and all control lines and information lines are not necessarily shown in the product. All configurations may be connected to each other.

What is claimed is:

1. A computer system comprising:
   at least one computer that includes a processor and a memory connected to the processor, wherein
   the memory stores:

model information for predicting an event of a target based on input data including a value of a plurality of feature quantities indicating a state of the target, and interpretation factor conversion information for managing an interpretation factor interpreting a basis of a prediction result for the input data, the interpretation factor being determined by a value of each of the plurality of feature quantities contained in the input data and a first evaluation value of the value of each of the plurality of feature quantities contained in the input data, the first evaluation value showing magnitude of contribution of the value of the feature quantity to a prediction result for the input data, and the processor is configured to:

calculate, when evaluation target data which is the input data to be evaluated is input, a prediction result for the evaluation target data based on the model information, calculate a first evaluation value of each of the plurality of feature quantities contained in the evaluation target data, specify a corresponding interpretation factor, based on the value and first evaluation value of each of the plurality of feature quantities contained in the evaluation target data, by referring to the interpretation factor conversion information, and generate display information for presenting the specified interpretation factor and output the display information.

2. The computer system according to claim 1, wherein the interpretation factor conversion information includes conversion data in which a set is associated with the interpretation factor, the set including, as elements, a combination of an area of the value of the feature quantity contained in the input data and an area of the first evaluation value of the feature quantity contained in the input data, and the processor is configured to:

specify an area including a value of each of the plurality of feature quantities contained in the evaluation target data, specify an area including a first evaluation value of each of the plurality of feature quantities contained in the evaluation target data, retrieve, by referring to the interpretation factor conversion information, the conversion data corresponding to a subset, the subset including, as elements, a combination of the area including the value of each of the plurality of feature quantities contained in the evaluation target data and the area including the first evaluation value of each of the plurality of feature quantities contained in the evaluation target data, and specify the interpretation factor from the retrieved conversion data.

3. The computer system according to claim 2, wherein the processor is configured to:

acquire area division information defining areas of the value and the first evaluation value of each of the plurality of feature quantities contained in the input data, acquire data for generation which is input data for generating the interpretation factor conversion information, calculate a prediction result of the data for generation and the first evaluation value of each of the plurality of feature quantities contained in the data for generation, generate subsets of the plurality of feature quantities contained in the input data, select a target subset from the subsets, calculate a second evaluation value showing magnitude of contribution of a combination of values of a plurality of feature quantities to a prediction result for the data for generation, the plurality of feature quantities being contained in the data for generation and being elements of the target subset, specify, when the second evaluation value is larger than a threshold, an area including the value of the feature quantity, based on the area division information, for the value of each of the plurality of feature quantities that are contained in the data for generation and are elements of the target subset, and specify an area including the first evaluation value of the feature quantity, based on the area division information, for the first evaluation value of each of the plurality of feature quantities that are contained in the data for generation and are contained in the target subset, generate a set as candidate conversion data, the set including the specified area of the values of the plurality of feature quantities and the specified area of the first evaluation values as elements, and generate the conversion data by associating the interpretation factor with the candidate conversion data and store the conversion data in the interpretation factor conversion information.

4. The computer system according to claim 3, wherein the processor is configured to:

acquire integration condition information defining a condition under which a plurality of pieces of the candidate conversion data is integrated, specify, based on the integration condition information, the plurality of pieces of candidate conversion data which are able to be integrated, integrate the plurality of pieces of specified candidate conversion data, and generate the conversion data by associating the interpretation factor with the plurality of pieces of integrated candidate conversion data.

5. The computer system according to claim 4, wherein the integration condition information includes a type and a threshold of an index indicating similarity between the candidate conversion data, and the processor is configured to:

calculate the index between the candidate conversion data, and specify, based on a comparison result of the index and the threshold, the plurality of pieces of candidate conversion data which are able to be integrated.

6. A method of presenting information on a prediction result of prediction for input data executed by a computer system, wherein:

the computer system includes at least one computer that includes a processor and a memory connected to the processor, the memory storing model information for predicting an event of a target based on input data including a plurality of feature quantities indicating a state of the target, and interpretation factor conversion information for managing an interpretation factor interpreting a basis of a prediction result for the input data, the interpretation factor being determined by a value of each of the plurality of feature quantities contained in the input data and a first evaluation value of the value of each of the plurality of feature quantities contained in the input data, the first evaluation value showing magnitude of contribution of the value of the feature quantity to a prediction result for the input data, the method of presenting information comprising:

a first step in which the processor is configured to calculate, when an evaluation target data which is the input data to be evaluated is input, a prediction result for the evaluation target data based on the model information;

a second step in which the processor is configured to calculate a first evaluation value of each of the plurality of feature quantities contained in the evaluation target data;

a third step in which the processor is configured to specify a corresponding interpretation factor, based on the value and first evaluation value of each of the plurality of feature quantities contained in the evaluation target data, by referring to the interpretation factor conversion information; and a fourth step in which the processor is configured to generate display information for presenting the specified interpretation factor and output the display information.

7. The method of presenting information according to claim 6, wherein the interpretation factor conversion information includes conversion data in which a set is associated with the interpretation factor, the set including, as elements, a combination of an area of the value of the feature quantity contained in the input data and an area of the first evaluation value of the feature quantity contained in the input data, wherein the third step includes:

a step in which the processor is configured to specify an area including a value of each of the plurality of feature quantities contained in the evaluation target data;

a step in which the processor is configured to specify an area including a first evaluation value of each of the plurality of feature quantities contained in the evaluation target data;

a step in which the processor is configured to retrieve, by referring to the interpretation factor conversion information, the conversion data corresponding to a subset, the subset including, as elements, a combination of the area including the value of each of the plurality of feature quantities contained in the evaluation target data and the area including the first evaluation value of each of the plurality of feature quantities contained in the evaluation target data; and a step in which the processor is configured to specify the interpretation factor from the retrieved conversion data.

8. The method of presenting information according to claim 7, further comprising:

a fifth step in which the processor is configured to acquire area division information defining areas of the value and the first evaluation value of each of the plurality of feature quantities contained in the input data;

a sixth step in which the processor is configured to acquire data for generation which is input data for generating the interpretation factor conversion information;

a seventh step in which the processor is configured to calculate a prediction result of the data for generation and a first evaluation value of each of a plurality of feature quantities contained in the data for generation;

an eighth step in which the processor is configured to generate subsets of the plurality of feature quantities contained in the input data;

a ninth step in which the processor is configured to select a target subset from the subsets;

a tenth step in which the processor is configured to calculate a second evaluation value showing magnitude of contribution of a combination of values of a plurality of feature quantities to a prediction result for the data for generation, the plurality of feature quantities being contained in the data for generation and being elements of the target subset;

an eleventh step in which the processor is configured to specify, when the second evaluation value is larger than a threshold, an area including the value of the feature quantity, based on the area division information, for the value of each of the plurality of feature quantities that are contained in the data for generation and are elements of the target subset, and specify an area including the first evaluation value of the feature quantity, based on the area division information, for the first evaluation value of each of the plurality of feature quantities that are contained in the data for generation and are contained in the target subset;

a twelfth step in which the processor is configured to generate a set as candidate conversion data, the set including the specified area of the values of the plurality of feature quantities and the specified area of the first evaluation values as elements; and a thirteenth step in which the processor is configured to generate the conversion data by associating the interpretation factor with the candidate conversion data and store the conversion data in the interpretation factor conversion information.

9. The method of presenting information according to claim 8, wherein the twelfth step includes:

a step in which the processor is configured to acquire integration condition information defining a condition under which a plurality of pieces of the candidate conversion data is integrated;

a step in which the processor is configured to specify, based on the integration condition information, the plurality of pieces of candidate conversion data which are able to be integrated; and a step in which the processor is configured to integrate the plurality of pieces of specified candidate conversion data, the thirteenth step includes a step in which the processor is configured to generate the conversion data by associating the interpretation factor with the plurality of pieces of integrated candidate conversion data.

10. The method of presenting information according to claim 9, wherein the integration condition information includes a type and a threshold of an index indicating similarity between the candidate conversion data, and the method of presenting information further comprising:

a step in which the processor is configured to calculate the index between the candidate conversion data; and a step in which the processor is configured to specify, based on a comparison result of the index and the threshold, the plurality of pieces of candidate conversion data which are able to be integrated.

\* \* \* \* \*